US006210873B1

(12) United States Patent
Sastry et al.

(10) Patent No.: US 6,210,873 B1
(45) Date of Patent: Apr. 3, 2001

(54) METHODS AND COMPOSITIONS FOR THE PRIMING OF SPECIFIC CYTOTOXIC T-LYMPHOCYTE RESPONSE

(75) Inventors: Jagannadha K. Sastry, Houston; Ralph B. Arlinghaus, Bellaire; Chris D. Platsoucas, Houston, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 07/800,932

(22) Filed: Dec. 2, 1991

Related U.S. Application Data

(63) Continuation-in-part of application No. 07/410,727, filed on Sep. 20, 1989, now Pat. No. 5,128,319, which is a continuation-in-part of application No. 07/090,646, filed on Aug. 28, 1987, now abandoned.

(51) Int. Cl.[7] .................................................. C12Q 1/70

(52) U.S. Cl. .............................. 435/5; 435/7.1; 435/7.24; 435/325; 435/974; 424/9.2; 424/184.1; 424/204.1; 424/207.1; 424/208.1

(58) Field of Search .................................. 435/5, 29, 32, 435/35, 724, 7.1, 7.24, 325, 974; 424/88, 93, 9.2, 184.1, 204.1, 207.1, 208.1

(56) References Cited

U.S. PATENT DOCUMENTS

| | | |
|---|---|---|
| 4,474,795 | 10/1984 | Aron et al. . |
| 4,493,795 | 1/1985 | Nestor, Jr. et al. . |
| 4,725,669 | 2/1988 | Essex et al. . |
| 4,818,527 | 4/1989 | Thornton et al. . |
| 4,943,628 * | 7/1990 | Rosen et al. ........................ 530/326 |
| 4,983,387 | 1/1991 | Goldstein et al. ..................... 424/88 |
| 5,013,548 | 5/1991 | Haynes et al. ........................ 424/89 |
| 5,019,387 | 5/1991 | Haynes et al. ........................ 424/89 |
| 5,030,449 | 7/1991 | Berzofsky et al. .................... 424/88 |
| 5,081,223 * | 1/1992 | Berzofsky et al. .................. 530/324 |
| 5,081,226 | 1/1992 | Berzofsky et al. .................. 530/324 |
| 5,108,744 * | 4/1992 | Deich et al. ........................... 424/92 |
| 5,128,319 | 7/1992 | Arlinghaus ............................ 514/12 |
| 5,142,025 | 8/1992 | Putney et al. ........................ 530/350 |
| 5,185,147 | 2/1993 | Papsidero ............................. 424/89 |

FOREIGN PATENT DOCUMENTS

| | | | |
|---|---|---|---|
| 0 267 802 | 5/1988 | (EP) | ............................ G01N/33/569 |
| 0 273 716 | 7/1988 | (EP) | ............................... C07K/8/08 |
| 0 284 587 | 9/1988 | (EP) | ............................... C07K/7/10 |
| WO 88/05051 | 7/1988 | (WO) . | |
| WO 89/03844 | 5/1989 | (WO) | ............................... C07K/7/04 |
| WO 89/07112 | 8/1989 | (WO) | ............................... C07K/7/08 |
| WO 90/00901 | 2/1990 | (WO) | ............................. A61K/39/00 |
| WO 91/04045 | of 1991 | (WO) . | |
| WO 91/01996 | 2/1991 | (WO) . | |
| WO 91/04051 | 4/1991 | (WO) | ............................. A61K/39/21 |
| WO 91/09869 | 7/1991 | (WO) . | |
| WO 91/13910 | 9/1991 | (WO) . | |
| WO 92/21377 | 12/1992 | (WO) . | |
| WO 93/04697 | 3/1993 | (WO) . | |
| WO 93/15750 | 8/1993 | (WO) . | |
| WO 93/18055 | 9/1993 | (WO) . | |
| WO 93/21218 | 10/1993 | (WO) . | |
| WO 94/00488 | 1/1994 | (WO) . | |

OTHER PUBLICATIONS

Sastry & Arlinghaus, "Identification of T–Cell Epitopes Without B–Cell Activity in the First and Second Conserved Regions of the HIV Env Protein," *Current Science*, 5(6):699–707, 1991.

Lasarte et al., "Induction of Cytotoxic T Lymphocytes in Mice Against the Principal Neutralizing Domain of HIV–1 by Immunization with An Engineered T–Cytotoxic–T–Helper Synthetic Peptide Construct," *Cellular Immunology*, 141:211–218, 1992.

Cohen, "AIDS Research Shifts to Immunity," *Science*, 257:152–154, 1992.

Sastry et al., "Rapid in Vivo Induction of HIV–Specific $CD8^+$ Cytotoxic T Lymphocytes by a 15–Amino Acid Unmodified Free Peptide from the Immunodominant V3–Loop of GP120," *Virology*, 188:502–509, 1992.

Berzofsky et al., "Epitopes of HIV and SIV. I. Host Responses," *Aids Res. Hum. Retroviruses*, 7(2):144, 1991.

Dadaglio et al., "Epitope Recognition of Conserved HIV Envelope Sequences by Human Cytotoxic T Lymphocytes," *J. Immunol.*, 147(7):2302–2309, 1991.

Gao et al., "Priming of Influenza Virus–Specific Cytotoxic T Lymphocytes Vivo by Short Synthetic Peptides," *J. Immunol.*, 147(10):3268–3273, 1991.

Houghten, Richard A., "Synthetic Heat–Stable Enterotoxin Polypeptide of *Escherichia coli* and Multimers Thereof," *Chemical Abstracts*, Abstract No. 50888r, 102:323, 1985, regarding WO 84/02,700, Scripps Clinic and Research Foundation.

Kemp et al., "Diagnostic and Antiviral Applications of Synthetic HIV–1 Peptides," In Peptides: Chemistry, Structure and Biology, Proceedings the Eleventh American Peptide Symposium, Jean E. Rivier and Garland R. Marshall, Eds., Jul. 9–14, 1989, La Jolla, CA.

Kloetzer et al., "Peptides of Feline Leukemia Virus Protein p15 E as Immunosuppressants and Vaccines," *Chemical Abstracts*, Abstract No. 90420x; 111:82, 1989, regarding WO 88/05,783, Ortho Pharmaceutical Corp.

(List continued on next page.)

*Primary Examiner*—Jeffrey Stucker
(74) *Attorney, Agent, or Firm*—Fulbright & Jaworski

(57) ABSTRACT

The present invention discloses a novel method for the rapid screening of candidate cytotoxic T lymphocyte- (CTL-) inducing compounds, such as peptides, by the in vivo priming of CTLs with synthetic peptides. The use of compounds so identified for the development of CTL vaccines for the treatment of various infectious disorders, including the treatment of viral diseases such as AIDS, herpes, influenza, and feline or bovine leukemia, is also disclosed, as is the use of this methodology for the preparation of specifically primed CTLs.

14 Claims, 9 Drawing Sheets

OTHER PUBLICATIONS

McMichael et al., "Peptide Fragments of Human Immunodeficiency Virus (HIV) for Stimulation of Cytotoxic T–Cell Immunity," *Chemical Abstracts,* Abstract No. 215075v, 112:487, 1990, regarding EP 346,022, Medical Research Counsel.

Shinnick et al., "Synthetic Polypeptides, Antibodies, Diagnostic Systems, and Kits for Immunological Detection of Infections with Tuberculosis Mycobacteria," *Chemical Abstracts,* Abstract No. 36241s, 108:496, 1988, regarding WO 87/01,118, Scripps Clinic and Research Foundation.

Takahashi et al., "A Single Amino Acid Interchange Yields Reciprocal CTL Specificities for HIV–1 gp160," *Science,* 246:118–121, 1989.

PCT Search Report dated Mar. 29, 1993.

Ellis, Ronald W., "New Technologies for Making Vaccines," *Vaccines,* W.B. Saunders Company, publisher. Stanley A. Plotkin, M.D. and Edward A. Mortimer, Jr., M.D., editors. Chapter 29, pp. 568–575, 1988.

Norley, Stephen and Kurth, Reinhard, "Vaccination against HIV," *Immunobiol.,* 184:193–207, 1992.

Rusche, James R. et al., "Antibodies That Inhibit Fusion of Human Immunodeficiency Virus–Infected Cells Bind a 24–Amino Acid Sequence of the Viral Envelope, gp120," *Proc. Natl. Acad. Sci. USA,* 85:3198–3202, 1988.

Ghiara et al., "Crystal Structure of the Principal Neutralization Site of HIV–1," *Science,* 264:82–85, 1994.

Takahashi et al., "Induction of Broadly Cross–Reactive Cytotoxic T Cells Recognizing an HIV–1 Envelope Determinant," *Science,* 255:333–336, 1992.

Rénia et al., "In Vitro Activity of $CD4^+$ and $CD8^+$ T Lymphocytes from Mice Immunized with a Synthetic Malaria Peptide," *Proc. Natl. Acad. Sci. USA,* 88:7963–7967, 1991. Published In USA.

Hart et al., "Priming of Anti–Human Immunodeficiency Virus (HIV) $CD8^+$ Cytotoxic T Cells In Vivo by Carrier–Free HIV Synthetic Peptides," *Proc. Natl. Acad. Sci. USA,* 88:9448–9452, 1991. Published in USA.

Schulz et al., "Peptide–Induced Antiviral Protection by Cytotoxic T Cells," *Proc. Natl. Acad. Sci. USA,* 88:991–993, 1991. Published in USA.

Sette et al., "A Microcomputer Program for Hydrophilicity and Amphipathicity Analysis of Protein Antigens," *Molec. Immunol.,* 23(8):807–810. Published in Great Britain.

Coates et al., "AIDS Vaccine Predictions," *Nature,* 326:549–550, 1987.

Margalit et al., "Prediction of Immunodominant Helper T cell Antigenic Sites from the Primary Sequence," *J. Immunol.,* 138(7):2213–2229, 1987.

DeLisi, C. and J. Berzofsky, "T–cell Antigenic Sites Tend to be Amphiphatic Structures," *Proc. Natl. Acad. Sci. USA,* 82:7048–7052, 1985.

Schild et al., Eur. J. Immunol., 21:2649–2654, 1991.
Maddox, J., Nature, 353:297, 1991.
Anderson, C., Nature, 353:287, 1991.
Kion, T. and Hoffman, G., Science, 253:1138–1140, 1991.
Kaneshima et al., Proc. Natl. Acad. Sci. USA, 88:4523–4527, 1991.
Clerici et al., J. Immunol., 146(7):2214–2219, 1991.
Freed et al., J. Virol., 65(1):190–194, 1991.
Freed & Risser, AIDS Res. Human Retroviruses, 7(10):807–811, 1991.
Murakami et al., BBA, 1079:279–284, 1991.
Berzofsky et al., FASEB J., 5:2412–1418, 1991.

Aichele et al., J. Exp. Med., 171:1815:1820, 1990.
Hosmalin et al., PNAS, 87:2344–2348, 1990.
Sastry & Arlinghaus, Hematologic Pathology, 4(3):157–159, 1990.
Cease et al., Proc. Natl. Acad. Sci. USA, 84:4249–4253, Jun. 1987.
International Patent Application WO86/06414, published Nov. 6, 1986.
International Patent Application WO85/00807, published Feb. 28, 1985.
European Patent Application 044710, published Jan. 27, 1982.
C&EN, 65:24 (1987).
Buller, et al., Nature, 328:77–79 (1987).
Barnes, Science, 236:1423–1425 (1987).
Barnes, Science, 237:128–130 (1987).
Salk, Nature, 327:473–476 (1987).
Newmark, Nature, 327:458 (1987).
Barnes, Science, 236:255–257 (1987).
Mitsuya and Broder, Nature, 325:773–778 (1987).
Modrow, et al., J. Virol., 61:570–578 (1987).
Chanh, et al., EMBO. Journal, 5:3065–3073 (1986).
Newmark, Nature, 325:290 (1987).
Gallo, Scientific America, Jan., 1987, pp. 47–56.
Livingstone and Fathman, Ann. Rev. Immunol., 5:477–501 (1987).
Milich and McLauchlan, Science, 234:1563–1566 (1986).
Walker, et al., Science, 234:1563–1566 (1986).
Bloom, Nature, 327:193 (1987).
Putney, et al., Science, 234:1392–1395 (1886).
Reiher, et al., Proc. Natl. Acad. Sci. USA, 83:9188–9192 (1986).
Lagrain, J. Virol., 60:1141–1144 (1986).
Earl, et al., Science, 234:728–731 (1986).
Maddon, et al., Cell, 47:333–348 (1986).
Robey, et al., Proc. Natl. Acad. Sci. USA, 83:7023–7027 (1986).
Zarling, et al., Nature, 323:344–346 (1986).
Milich, et al., J. Exp. Med., 164:532–547 (1986).
Kennedy, et al., Science, 231:1555–1559 (1986).
Berzofsky, Science, 229:932–940 (1985).
Hopp, Mol. Immunol., 21:13–16 (1984).
Shinnick, et al., Ann. Rev. Microbiol., 37:425–446 (1983).
Austin American–Statesman, Mar. 26, 1987.
Kast er al., PNAS, 88:2283–2287, 1991.
Sastry & Arlinghaus, Curr. Sci., 5:699–707, 1991.
LaRosa et al., Science, 249:932–935, 1990.
Emini et al., J. Virol., 64(8):3674–3678, 1990.
Scott et al., PNAS, 87:8597–8601, 1990.
Javaherian et al., PNAS, 86:6768–6772, 1989.
Devash et al., PNAS, 87:3445–3449, 1990.
Palker et al., PNAS, 85:1932–1936, 1988.
Takahashi et al., PNAS, 85:3105–3109, 1988.
Takahashi et al., J. Exp. Med., 170:2023–2035, 1989.
Takahashi et al., J. Exp. Med., 171:571–576, 1990.
Berzofsky et al., Nature, 334:706–708, 1988.
Bevan, Nature, News and Views, 342:478–479, 1989.
Deres et al., Nature, 342:561–564, 1989.
Cleric et al., Nature, 339:383–385, 1989.
Howell et al., Science, 246:668–670, 1989.
Arthur et al., J. Virol. 63(12):5046–5053, 1989.
Bio/Technology, In the News, 6:345, 1988.
Barnes, Science, Research News, 241:533–534, 242:515, 1988.

Takeda et al., Science, 242:580–583, 1988.
Homay et al., Science, 244:1357–1360, 1989.
Miller, Nature—News and Views, 332:109–110, 1988.
Patarroyo et al., Nature 332:158–161, 1988.
Maddon et al., PNAS, 84:9155–9159, 1987.
Sternberg et al., FEBS Letts., 218(2):231–237, 1987.
Nara et al., PNAS, 84:3797–3801, 1987.
Wain–Hobson et al., Cell, 40:9–17, 1985.
International Search Report.
Deres et al "In Vivo Priming of Virus–specific Cytotoxic T Lymphocytes with Synthetic Lipopeptide vaccine." *Nature* vol. 342 Mar. 11, 1989.*
Kast et al "Protection against lethal Sendri Virus Infection by in Vivo Priming of virus–specific Cytotoxic T Lymphocytes with a Free Synthetic Peptide" *PNAS* vol. 88 pp. 2283–2287 (Mar. 1991).*
White et al (1986) Medical Virology, 3$^{rd}$ ed. Academic Press, Orlando, Fla. p. 283–293.*
Walker et al (Apr. 1988), Science 240:64–66.*
Koenig et al (Nov. 1988) PNAS 85:8638–8642.*
Nixon et al (Dec. 1988) Nature 336:484–487.*
Clark (1980) The Experimental Foundations of Immunology, J Wiley & Sons, NY pp. 278–283.*

Livingstone et al (1987) The Structure of T–Cell Epitopes. Ann Rev Immunol 5:477–501.*

Milich et al (1986) Non overlapping T and B Cell . . . J Exp Med 164:532–547.*

Watari et al (1987) A Synthetic Peptide Induces . . . J Exp Med 165:459–470.*

Coates et al (1987) AIDS Vaccine Predictions Nature 326:549–550.*

Sternberg et al, (1987) Prediction of Antigenic Determinants FEBS Letters 218:231–237.*

Gray (1977) Gray's Anatomy, Bounty Books (NY) pp. 623–637.*

Shinnick et al (1983) Synthectic Peptide Immunogens . . . Ann. Rev. Microbiol. 37:425–446.*

Zarling et al (1986) T–cell responses to human AIDS Virus . . . Nature 323:344–346.*

Earl et al (1986) T–Lymphocyte Priming . . . Science 234:728–731.*

* cited by examiner

PROLIFERATION OF PLN CELLS
FROM IMMUNIZED BALB/C MICE

METHODS AND COMPOSITIONS FOR THE PRIMING OF SPECIFIC CYTOTOXIC T-LYMPHOCYTE RESPONSE

This is a continuation-in-part of application Ser. No. 07/410,727, filed Sep. 20, 1989, now U.S. Pat. No. 5,128,319, which was a continuation-in-part of Ser. No. 07/090,646, filed Aug. 28, 1987, now abandoned.

The government may own certain rights in the present invention pursuant to NIH grants AI-29308.

BACKGROUND OF THE INVENTION

1. Field of the Invention

The present invention relates to methods and compositions for the priming of a specific cytotoxic T-lymphocyte (CTL) response, and to the use of these methods in the identification of candidate substances, typically polypeptides, for use in the preparation of CTL vaccines having the ability to prime an in vivo CTL response. This technology will have particular application in the prevention and treatment of viral diseases, such as AIDS, herpes, influenza, feline leukemia, and the like.

2. Description of the Related Art

AIDS was first recognized in the United States in 1981; the number of cases has been increasing at a dramatic pace since then. Since 1978 more than 2.4 million AIDS infections have been reported in the United States, alone (Rees, 1987). Once significant immunosuppressive symptoms appear in an infected individual, the expected outcome of the infection is death. There is currently no known treatment that can indefinitely delay or prevent the fatal consequences of the disease. Although the disease first manifested itself in homosexual or bisexual males and intravenous drug abusers, it has now spread to others by means such as intimate sexual contact with or receipt of blood products from a carrier of the virus.

The causative agent, associated with AIDS has been identified as a group of closely related retroviruses commonly known as Human T Cell Lymphotrophic Virus-type III (HTLV-III), Lymphadenopathy Viruses (LAV), AIDS-Related Viruses (ARV), or more recently named Human Immunodeficiency Virus (HIV). These viruses will be collectively referred to herein for convenience as HIV.

Like other retroviruses, HIV has RNA as its genetic material. When the virus enters the host cell, a viral enzyme known as reverse transcriptase copies the viral RNA into a double stranded DNA. The viral DNA migrates to the nucleus of the cell where it serves as a template for additional copies of viral RNA which can then be assembled into new viral particles. The viral RNA can also serve as messenger RNA for certain viral proteins [either the viral core proteins (known as p18, p24 and p13)] or the reverse transcriptase, or be "spliced" into specific viral messenger RNAs necessary to produce several other viral proteins including two glycosylated structural proteins known as gp41 and gp120 which are inserted in the outer membrane of the virus (Wain-Hobson et al., 1985). A recent study has shown that purified gp120 induces antibody in the goat, horse and rhesus monkey that neutralizes HIV in lab tests (Robey et al., 1986).

Vaccines have been used for many years to prevent infections caused by agents such as viruses. The general approach has been to inject healthy individuals with, for example, a killed or modified virus preparation in order to prime the individual's immune systems to mount an assault on the infecting virus. Recent advances in recombinant DNA technology have allowed safer methods of vaccination that involve use of exposed viral components produced by microbial systems. After sufficient purification, the viral component, for example a protein subunit, is administered as a vaccine in a suitable vehicle and/or an adjuvant. The latter stimulates the host's system in a way that improves the immune response to the viral subunit.

Another potential method of making a vaccine is by using chemically synthesized peptide fragments of a viral protein subunit. This method has several advantages over the other methods of producing vaccines, including purity of the product, reproducibility and specificity of the immune response.

Surface antigens of an infecting virus can elicit T cell and B cell responses. From the work of Milich and coworkers (Milich et al., 1986; Milich & McLachlan, 1986) it is clear that some regions of a protein's peptide chain can possess either T cell or B cell epitopes. These epitopes are frequently distinct from each other and can comprise different peptide sequences. Other examples include the work of Maizel et al., (1980) for hen egg-white lysozyme, and Senyk et al., (1971) for glucagon. Thus, short stretches of a protein sequence can elicit a T cell response but not a B cell response. A more complete review of these and other observations pertinent to this point is included in the work of Livingstone & Fathman (1987).

A short peptide region within the surface protein of infectious Hepatitis B virus has been shown to elicit only a T cell response in mice (Milich et al., 1986). Specifically, a synthetic peptide, whose sequence is derived from amino acids numbered 120–132 located within the pre-S(2) domain of the Hepatitis B surface antigen gene, elicited a very strong T cell priming response to the peptide but stimulated only a very weak antibody response. In other words, mice mounted a poor antibody response to that peptide, but the T cells of immunized mice were efficiently primed (i.e. activated) to recognize that peptide as measured in T cell proliferation assays (Milich et al., 1986). The low level of the antibody produced by mice immunized with this peptide did not bind to the native viral surface antigen.

In contrast to the above-described results, a second peptide sequence (amino acids 132–145) elicited a very weak T-cell response in mice (Milich et al., 1986). This second peptide did, however, efficiently bind antibody raised against it under conditions where a T cell epitope is provided.

Mice were also immunized with a longer peptide made up of both of the above-mentioned T- and B-active peptide sequences. In this case, high titers of antibody were produced against the B site peptide but not the T site peptide. The combination of both T- and B-sites within one peptide should stimulate both T and B cell responses, as measured by producing a specific antibody to the B cell epitope of the peptide chain. Synthetic peptide antigens may be constructed to produce two types of immune responses: T-cell only and T cell combined with a B cell response.

Cellular immune responses provide a major mechanism for reducing the growth of virus-infected cells (Doherty et al., 1985). A report by Earl et al., (1986) demonstrated T-lymphocyte priming and protection against the Friend virus (a retrovirus)-induced mouse leukemia by a viral surface protein vaccine. Direct evidence for the role of a subset of T-lymphocytes (OKT8/LEU2 positive) in suppressing HIV growth in vitro was recently obtained by Walker et al. (1986). This study further demonstrated that, after depletion of CD8$^+$ T-lymphocytes from the blood of HIV-infected individuals, large quantities of HIV were isolated from peripheral blood mononuclear cells of four of seven asymptomatic, seropositive homosexual men who were initially virus-negative or had very low levels of virus. Thus, the CD8+ cytotoxic T-lymphocytes (CTLs) may play a role in virus infected individuals to prevent HIV replication and disease progression.

The concept of identifying T-cell epitopes in proteins for inclusion in potential vaccine candidates has gained importance as a result of the demonstration by Townsend et al. (1986) that CTL epitopes of influenza nucleoprotein can be defined by short synthetic peptides. However, to date there are only three documented cases (Deres et al., 1989; Aichele et al., 1990; Kast et al., 1991) that describe the use of synthetic peptides in the in vivo priming of CTLs, these relate to influenza, Sendai and lymphocyte choriomeningitis viruses. In each of the above cases, the immunization protocols are cumbersome, require either modifications of peptides or many immunizations to be carried out to demonstrate CTLS, and do not lend themselves to the rapid screening of a large number of candidate substances. For example, the method of Aichele and colleagues (1990) involves three immunizations at one week intervals by the subcutaneous route, and takes four weeks before potential CTLs are obtained for assaying.

Candidate CTL epitopes in both structural and regulatory HIV proteins have been proposed (Takahashi et al., 1988; Nixon et al., 1988) but none of these have been shown to be capable of inducing virus-specific CTLs in vivo (Berzofsky, 1991). For example, although the peptide RIQRG-PGRAFVTIGK has been identified as a CTL epitope (Takahashi et al., 1988), in these studies the in vivo induction of RIQRGPGRAFVTIGK-specific CTLs was accomplished by infecting Balb/c mice with recombinant vaccinia virus expressing HIV env proteins (Takahashi et al., 1988) and attempts at immunization with free peptide have been unsuccessful (Berzofsky, J. A., 1991).

There is thus clearly a need for techniques for the rapid identification of CTL-reactive epitopes that have the ability to prime a specific T-cell response. Previous methods have suffered a number of drawbacks, most notably, their requirement for multiple injections of material to be tested, a wait of up to 3 weeks or longer to determine whether the substance had a positive effect on CTL response, and the general need to include a modifier with the substance being tested in order to elicit a response. Clearly, a rapid method for the delineation of peptides with an in vivo CTL inducing capacity is of vital importance in the design of preventative and therapeutic strategies in relation to disease such as AIDS.

SUMMARY OF THE INVENTION

The present invention addresses one or more of the foregoing or other disadvantages in the prior art by providing immunization and assay methods for the rapid and sensitive screening of a large number of candidate compounds, such as peptides, to identify those having the ability to specifically prime a CTL response, and therefore most appropriate for use in therapeutic compositions such as CTL vaccines. The invention therefore concerns generally methods and compositions for the preparation of vaccines which include as one of their components, a compound or compounds having the ability to specifically prime CTL to render them reactive against cells harboring infectious agents such as viruses.

In a general sense, the method of the present invention involves assaying a composition for its ability to induce a cytotoxic T cell response in an animal, and includes generally immunizing an animal, such as a human subject or an experimental animal such as a mouse, rat, rabbit, guinea pig, goat, rhesus monkey, or chimpanzee, thereafter collecting cells from lymph nodes or other lymphoid tissue from the animal, and then testing the tissue for the presence of CTLs that are primed to kill or lyse cells producing a component of an infectious agent, such as a viral envelope, core protein, one of the functional proteins (e.g., reverse transcriptase) or the like.

Thus, the method of the invention includes generally three steps, with the first step involving immunizing an animal with the composition to be tested. While it is believed that any accepted mode and route of immunization can be employed and nevertheless achieve some advantages in accordance herewith, the inventors have found particular advantages to be associated with intradermal immunization. Intradermal immunization is believed to be preferred because it serves to activate more efficiently the cell mediated arm of the immune system. Moreover, although where desired one may choose multiple injections of the immunizing substance, and even multiple sites of injection, the inventors have found that a particular advantage of the invention is that a single injection of the candidate will usually be sufficient to achieve detectable CTL activation in a nearby lymph node. Furthermore, although where desired one may employ immunization modifiers such as T-helper cell peptide sequences, lipid structures that induce micelle formation, peptide polymerization methods, or the like in association with the candidate composition, the inventors have found that the sensitivity of the assay is such that the use of such modifiers will generally not be required in order to achieve CTL priming.

Once immunization has been effected, it will then be necessary to recover cytotoxic T cells from lymphoid tissue of the immunized animal. The preferred lymphoid tissue will be lymph node tissue, and most preferrably tissue from draining lymph nodes proximal to the site of injection. As used herein, the word "proximal node" is intended to refer to the node or nodes that are located proximal to the site of injection, e.g. the popliteal node of the mouse following foot pad injection. It is believed that the use of proximal or draining nodal tissue to identify CTL activation is one reason for the rapidity of the more preferred aspects of the invention. Such nodes are physically located in the proximity of the immunization site, or in the area draining the site of immunization, and also included are those draining nodes that are physically at a greater distance from the immunization site.

The final step of the assay in its most general sense involves determining whether said cytotoxic T cells have been activated by the composition. Although it is not generally required, it will typically be preferred to actually measure the level of activation, through, e.g., radioactive chromium-release assays, or other radioisotope assays, or single cell assays; also single cell cytotoxic assays using vital stains and/or cell-sorters could be employed.

Where measurement of activation of cytotoxic T cells is desired, a preferred method involves contacting a killing effective amount of said cytotoxic T cells with MHC-matched target cells that exhibit the candidate epitope on their cell surfaces; maintaining said contact for a time period sufficient for said cytotoxic T cells to lyse said target cells; and determining the degree of T cell-mediated lysis of said target cells. However, any method capable of detecting a specific CTL response may be employed, including but not limited to chromium-release assays, single-cell assays or even determination of cell-cell conjugates.

An advantage of the present invention is the speed with which one is able to determine the ability of the candidate substance to activate CTLs. Prior techniques have generally required a wait of a few weeks (Kast et al., 1991; Aichele et al., 1990). The present technique, though, typically requires only about 7 to 10 days following immunization. The reason for the reduced time necessary to achieve a CTL response with the assay of the present invention is believed to be the result of the route of immunization and the use of draining or proximal lymph node cells. A further advantage is the ability to test peptide candidates without the use of an associated modifier, such as carrier molecules, lipid tails, or T helper epitopes, to enhance its CTL activity.

Typically, the composition to be tested for CTL priming capability will comprise one or more peptides, or peptide multimers, believed to have or suspected of having useful activities. Through the application of the techniques of the present invention to such peptides, one will thus be enabled to determine whether such peptides do in fact have CTL priming activity. If so, then the peptide will be a candidate for inclusion in a CTL priming vaccine. It will be appreciated by those of skill in the art that while candidates for CTL priming activity will generally comprise peptides (or proteins), the use of the assay of the present invention in the context of non-peptidyl compounds is certainly not excluded.

It is proposed that the method of the present invention will find a broad range of application, particularly in the identification of components for use in the preparation of vaccines for the treatment and/or prevention of viral diseases such as AIDS, influenza, feline leukemia, bovine leukemia, Herpes virus infections, and even in the case of non-viral infectious diseases such as parasitic and bacterial infections. Therefore, in the case of embodiments directed to the identification of epitopes for promoting a specific anti-HIV CTL response, the invention will generally be concerned with the identification of peptides having the ability to direct a CTL response to HIV-infected cells.

In the context of vaccine development, the method will include first identifying a CTL-reactive composition in accordance with the foregoing method, and admixing the composition with one or more pharmaceutically acceptable diluents or additives, such as water, salts, emulsifiers and/or adjuvants. Of course, the amount of the composition added to the vaccine will vary depending on its ability to induce a specific CTL response, it solubility, and other biological responses. The selection of an appropriate amount of the identified CTL-priming composition will therefore be well within the skill of the art in light of the present disclosure.

In other embodiments, the invention involves a method of preparing cytotoxic T cells. In its most general sense, this method includes immunizing, preferrably intradermally, an animal with a composition having the ability to induce a cytotoxic T cell response to a preselected epitope of a targeted protein. The epitope or epitopes employed may or may not be specific for CTL priming, and thus may or may not substantially induce antibodies that will cross react with the targeted protein. However, in the practice of this aspect of the invention, one will typically desire to recover cytotoxic T cells from lymph nodes of the animal for further use. Numerous potential uses of specifically primed CTLs are envisioned. For example, in the case of human therapy, it is contemplated that specifically primed CTLs may be cultured and administered to humans for the treatment of viral infections or patients with cancer. In this case, the CTLs are prepared by immunizing the species in vivo and isolating the immune cells to expand in vitro in the presence of appropriate peptide, cytokines and presenting cells.

Typically, for the induction of an HIV-directed CTL response, the invention will involve the use of peptides which comprise from 7 to about 30 amino acid residues, and have a sequence that corresponds to a domain of an HIV protein such as the gp160 envelope and core proteins, reverse transcriptase, tat, rev or other gene products expressed by the virus, which peptide includes within its structure a conserved region.

For the preparation of vaccines, peptide multimers are generally preferred in order to include multiple CTL epitopes within a single complex. Two specific classes of peptide multimers are disclosed. In one class, the amino-terminal residue of a peptide is peptide-bonded to a spacer peptide that contains an amino-terminal lysyl residue and one to about five amino acid residues such as glycyl residues to form a composite polypeptide. Those added residues of the spacer peptide do not interfere with the immunizing capacity of the multimer, nor with its capacity to form surfactant-like micelles in aqueous compositions. The alpha- and epsilon-amino groups of the amino-terminal lysyl residue are amidified with a $C_{12}$–$C_{18}$. Fatty acid such as palmitic acid to form the reaction product that is used. The di-amide so formed forms surfactant-like micellular multimers in an aqueous composition.

A second class of multimer is a polymer having a peptide as a repeating unit. Here, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimers in which the peptide repeating units are linked by cystine (oxidized cysteine) residues.

A peptide multimer of either class can contain one or a plurality of different peptide sequences. A peptide of a multimer is an "active" peptide in that when used in a composition discussed below, the multimer can induce cell mediated immunity such as production of cytotoxic T cells. A multimer can also include an inactive peptide, for example to assist in dispersing the multimer in the aqueous medium. The lysyl-containing peptide spacer discussed before can be viewed as such an inactive peptide.

The peptide multimer is utilized in an aqueous composition (inoculum). That composition contains water having a before-described multimer dispersed therein. The composition, when used to immunize an immunocompetent host animal such as a mouse, has the capacity of inducing cell mediated immunity such as cytotoxic T cell activation to the native HIV protein corresponding in sequence to that of an active peptide of the multimer, but does not substantially induce production of antibodies that immunoreact with that corresponding native HIV protein. The composition thus contains an immunizing effective amount of a before-discussed multimeric peptide.

DETAILED DESCRIPTION OF THE PREFERRED EMBODIMENTS

Figure 1:
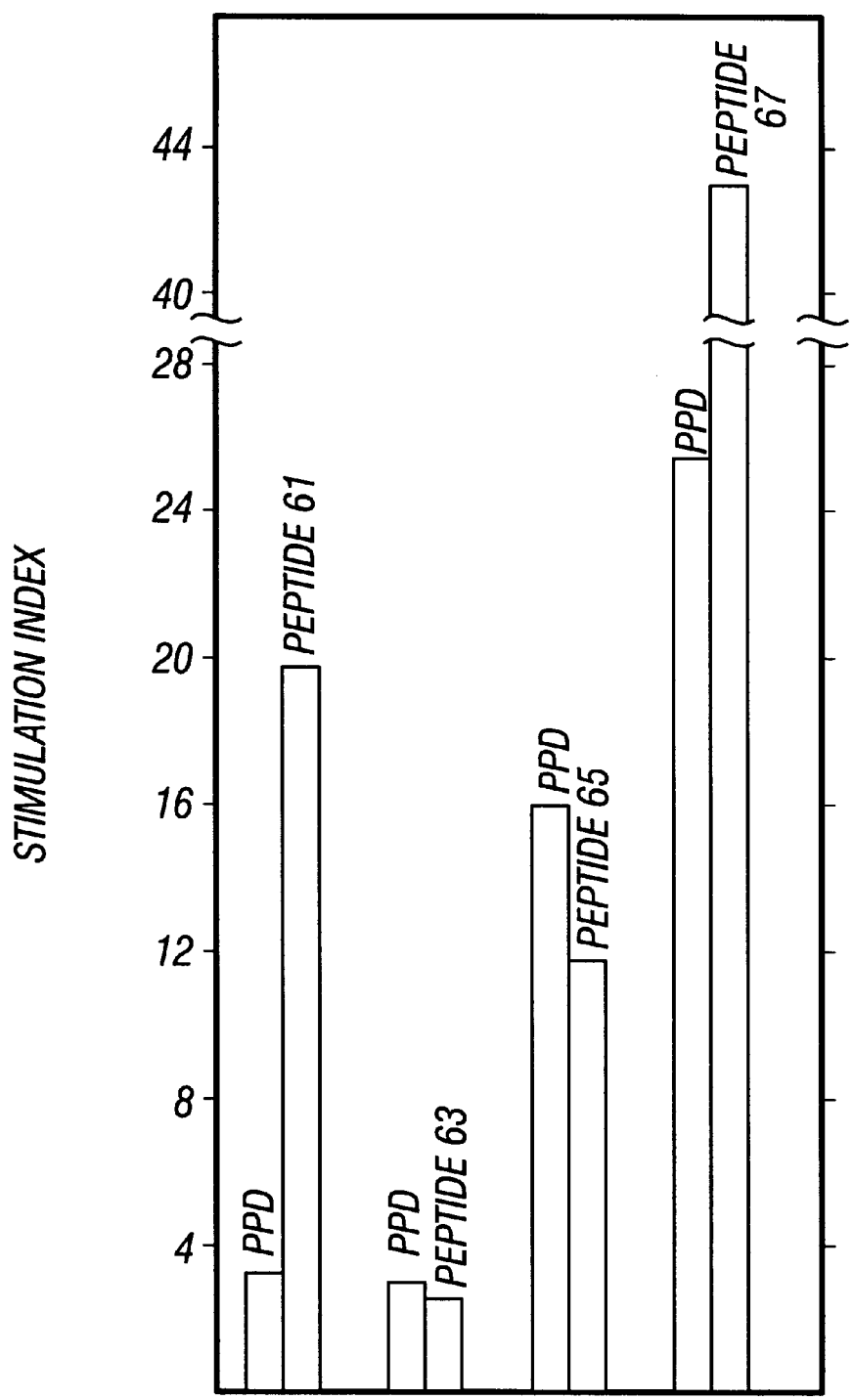
FIG. 1. The in vitro proliferation of popliteal lymph node (PLN) cells after in vivo immunization of Balb/c mice. Balb/c mice were immunized with an aqueous composition containing an immunologically effective amount of a peptide multimer polymer of this invention prepared from each of peptides 61, 63, 65 and 67. Tuberculin purified protein derivative (PPD) was used as a control, as shown. A $^3$H-thymidine ($^3$H-TdR) incorporation assay was used for these studies. The data are illustrated as a stimulation index, which is calculated as the fold increase in radioactivity counts in the presence of the peptide antigen compared to background values where no antigen was added. Details of this study are discussed hereinafter.
Figure 2:
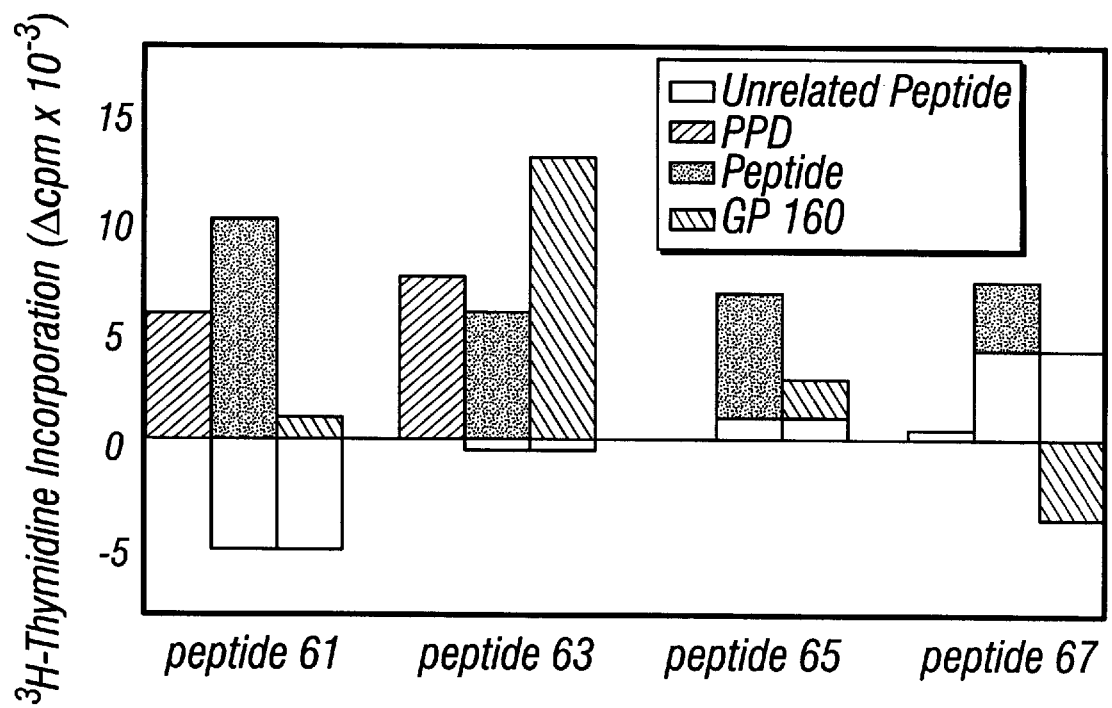
FIG. 2. T cell proliferation ($^3$H-TdR incorporation) of PLN cells after immunization of B6C3 F1 mice with an aqueous composition containing an immunologically effective amount of a peptide multimer polymer of this invention prepared from each of peptides 61, 63, 65 and 67. An unrelated peptide, PPD and gp160 were used as controls. The data are shown as the $^3$H-TdR incorporation [delta (Δ) counts per minute (cpm)] obtained by subtracting radioactivity values in control wells without added antigen from those in wells with antigen. Details of this study and those of the studies of FIGS. 3–5 are discussed hereinafter.
Figure 3:
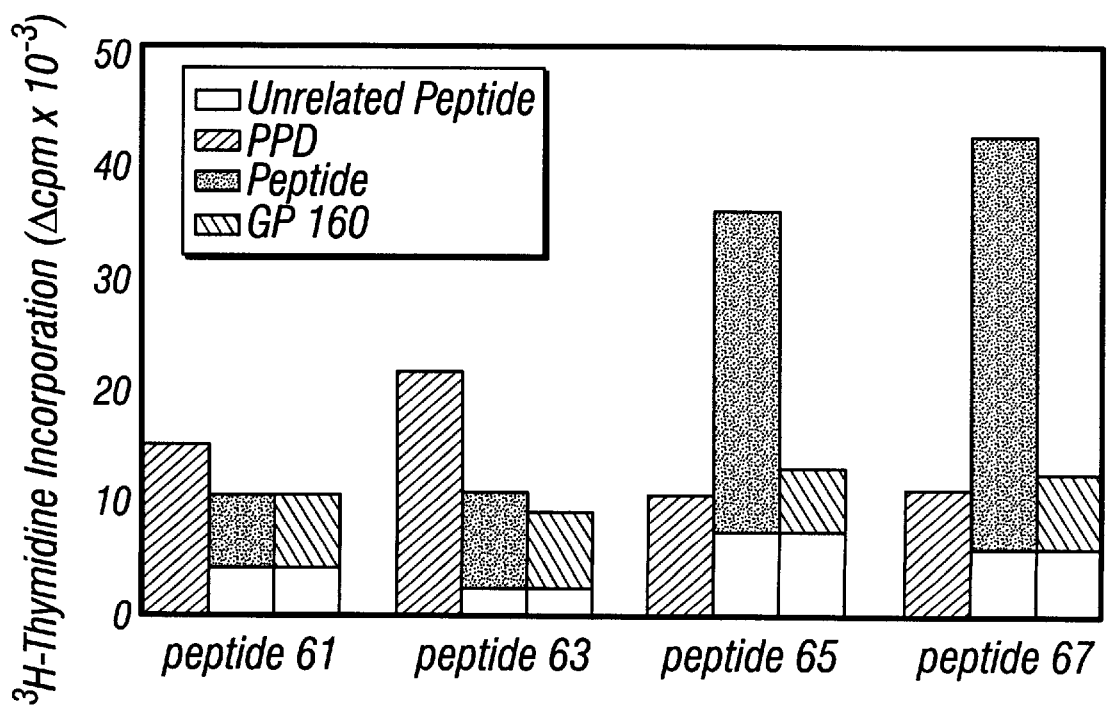
FIG. 3. As in FIG. 2, except A.SWxBalb/c F1 mice were utilized as the animal hosts.
Figure 4:
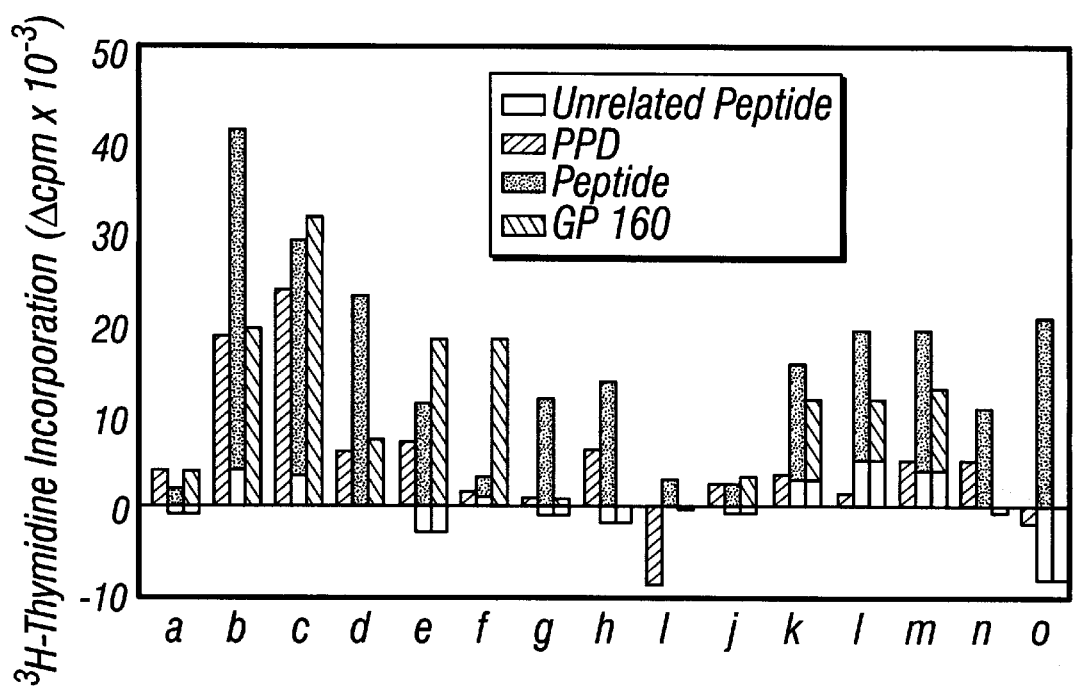
FIG. 4. As in FIG. 2, but using multimers prepared from peptides 103 through 117 (a through o, respectively) to immunize B6C3 F1 mice.
Figure 5:
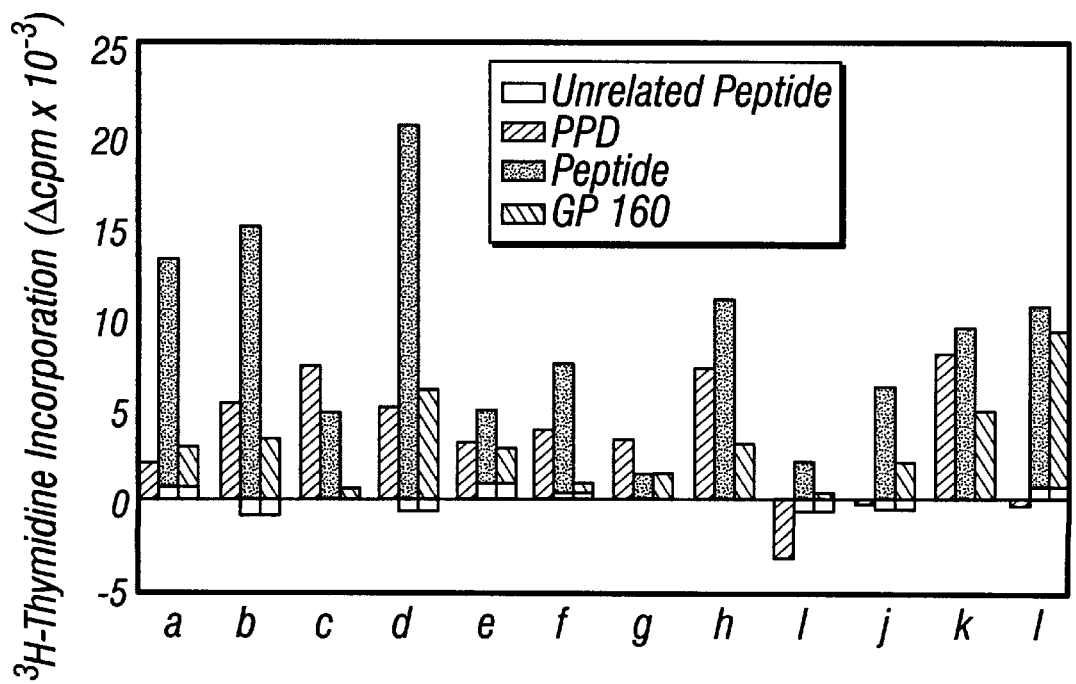
FIG. 5. As in FIG. 4, except that A.SWxBalb/c mice were again used as the animal hosts.

The present invention thus concerns in one embodiment a novel and rapid method for screening candidate compounds, such as peptides or multimers thereof, to identify appropriate CTL-inducing active compounds for use, e.g., in CTL vaccines. In preferred screening procedures, candidate peptides or peptide multimers are assayed for in vivo CTL-induction by injecting the test substance into an experimental animal, recovering T cells from the lymph nodes and measuring the activity (priming) of such CTLs. Most preferrably immunization would involve a single intradermal injection of the test peptide in complete Fruend's adjuvant (CFA) into an appropriate site, such as the hind-foot pad of a mouse, recovering lymph node T cells, preferrably from the draining popliteal lymph nodes (PLN), and determining their CTL activity by assaying the T cell-mediated lysis of MHC-matched target cells decorated with the candidate peptide or expressing the parent protein. This procedure allows the results to be obtained only 8–10 days after immunization.

Employment of such a screening procedure will result in the identification of T cell active peptides, whether they be peptides that induce substantially only a CTL response, or also induce an antibody response (i.e., B cell reactive). A plurality of strains of mice that vary in their histocompatibility genes are used for these screenings. Peptides that have a broad response in the various MHC genotypes are selected for further study in primates, and finally humans. Exemplary assay procedures are found hereinafter.

The synthesis of the candidate peptides to be tested in the present invention can be conducted using an automated peptide synthesiser. For example, peptides can be synthesised using the Merrifield solid phase method (Merrifield, 1963) either on a modified Vaga 250 automatic peptide synthesizer or by the "Bag" method, as described by Houghton et al. (1985). Following the synthetic reactions, the completed peptides are then recovered. In the above two methods this involves the removal of the T-BOC blocking groups and hydrolysis of the peptide from the resin using hydrofluoric acid (HF) treatment at 0° C. for 1 hour. The various organic by-products can then be removed, for example by extraction with ether, and the peptides extracted from the supporting resin with a reagent such as 25% acetic acid.

The compounds to be tested for potential CTL-inducing properties are then used to immunise an experimental animal, such as a mouse, rat, rabbit, guinea pig, goat, Rhesus monkey, chimpanzee, or the like. In the rapid screening method for the identification of appropriate CTL-inducing candidate compounds, the inventors have found that the intradermal immunization of a mouse can be advantageously employed. Intradermal immunization is believed to be particularly effective as it serves to efficiently activate the cell mediated limb of the immune system. The inventors have found that even more advantageous aspects of this immunisation protocol are (i) that a single injection of the candidate will usually be sufficient to achieve detectable CTL activation, and (ii) that the sensitivity of the assay is such that the use of immunisation modifiers will generally not be required in order to achieve CTL priming.

Accordingly, in preferred screening embodiments, mice are immunized by intradermal injection into the hind footpad with an appropriate composition, such as 100 μg of the test peptide in a 1:1 emulsion with complete freund's adjuvant (CFA). After a period of time sufficent to induce a CTL response, such as 10 days, the draining popliteal lymph nodes (PLN) are surgically removed and the cells were separated by mild homogenization. The PLN cells thus obtained, typically between $10-50 \times 10^6$ cells/lymph node/mouse, are maintained in 5–10 ml of a solution such as Click's medium, 10% FCS, 50 μM 2-mercaptoethanol, and re-stimulated for 5 days, in vitro, with irradiated (3300 rads) syngeneic mouse spleen cells pre-treated with the candidate peptide. A syngeneic cell expressing the parent protein from which the peptide is derived, such as the HIV gp160 protein, would be an appropriate target cell. However, the inventors contemplate that peptide-decorated spleen cells which can be easily generated, for example by pre-treating the cells with the peptide monomer at a concentration of approximately 40 μg/ml for 2 hours at 37° C., may be preferred for use in accordance with the present invention.

The re-stimulated effector cells are then washed, for example with RPMI 1640 medium, 10% FCS, resuspended at an appropriate cell density in the region of $5 \times 10^6$/ml, and assayed for CTL activity. A suitable method of assaying for CTL activity is to determine the release of a non-metabolisable radiolabeled substance from specific target cells which have been pre-loaded with the substance. Measuring the release of $^{51}$Cr from peptide-treated syngeneic cells, as described by Platsoucas & Good (1981), is considered by the inventors to be a particularly suitable method.

To generate peptide-expressing target cells for use in the CTL assay, appropriate syngeneic cells, such as P815 cells, are first loaded with radioactive compound such as chromium. This can be achieved by incubating the cells for 2 hours at 37° C. with 250 μCi of $^{51}$Cr. The cells are then washed three times and incubated for an additional 2 hours at 37° C. with the monomeric form of the test peptide at a concentration of approximately 40 μg/ml. The cells are then washed twice with a solution such as RPMI medium, 10% FCS, and then resupended at an appropriate concentration, for example in the region of $5 \times 10^4$ cells/ml. The target cells thus generated can then be employed in the CTL assay, for example by mixing them with the candidiate effector cells in U-bottom 96 well-microtiter plates such that different effector to target cells (E:T) ratios are achieved.

Alternatively, as discussed above, target cells expressing the parent protein from which the test peptide was derived can be generated and used in the CTL assay. In this method, syngeneic cells are infected for 18–20 hours with an appropriate amount, such as $5 \times 10^7$ plaque forming units, of recombinant vaccinia virus containing the gene for the parent protein which is to be expressed. As a control, syngeneic cells may be infected with recombinant vaccinia virus which carries the gene for an immunologically unrelated protein. At this stage one may wish to confirm the presence of the required protein in the target cells, but not in the control cells, for example by western blotting both infected cell types with specific antibodies. Target cells created in this manner can then be labelled with the radioactive compound, in this case 100 μCi of $^{51}$Cr, and used in the chromium release CTL assay (Platsoucas & Good, 1981), as described above.

In certain embodiments where the candidate peptides to be screened are derived from the HIV protein gp160, the recombinant vaccinia virus system can be used to prepare cells which specifically express this protein. For use in this regard, the inventors have found the control (VSC8) and HIV env-expressing (VPE16) recombinant vaccinia viruses obtained through Dr. Bernard Moss via the AIDS Research and Reference Reagent Program, (Division of AIDS, NIAID, NIH) to be of particular use. To confirm the presence of the gp160 protein in such VPE16-infected P815 target cells, the inventors found it convenient to employ HIV antibody-positive human sera in the western blotting experiments. In using the VPE16-infected P815 target cells in CTL assays, the inventors determined that it was particularly advantageous to employ $5 \times 10^4$ target cells/ml and $1 \times 10^6$ candidate CTL effector cells/ml, mixed so as to obtain an initial E:T ratio of 20:1.

In CTL assays conducted using either of the above target cells, the percentage specific $^{51}$Cr-release can be calculated as:

$$100 \times (\text{experimental release} - \text{spontaneous release})/(\text{maximum release} - \text{spontaneous release})$$

The maximum release can be determined by measuring the radioactivity released into the supernatant from target cells in which complete lysis has been experimentally induced, such as by using a 5% solution of the non-ionic detergent Triton X-100 to disrupt the membranes of the cells. Spontaneous release can be determined by measuring the radioactivity released into the supernatant from target cells incubated without added effector cells. It is contemplated that valid experiments will have a value for spontaneous target lysis which is between 15–20% of the maximum lysis observed.

Prior to assaying the PLN cells for possible CTL activity, one may desire to first deplete certain cell populations, such as CD4$^+$ or CD8$^+$, from the mixture of cells. In this regard, re-stimulated PLN cells can be treated with either anti-CD4 monoclonal antibody (clone GK-1.5) plus complement (C) (+ anti CD4+C), or anti-CD8 monoclonal antibody (clone 53–6.72) plus C (+anti CD4+C), as described by Platsoucas & Good (1981). It may also be desirable to treat certain PLN cells with complement alone (+C), to act as a comparison. Cells treated in any of these ways can then tested for their capacity to lyse MHC-matched target cells that have been pre-treated with the monomeric form of the peptide or infected with recombinant vaccinia virus expressing the parent protein from which the test peptide was derived.

Where one desires to identify CTL reactive compounds that do not exhibit an antibody generating capability, peptides identified as being T cell active may be screened to identify those that lack B cell stimulatory activity. Such peptides are proposed to be particularly useful in the preparation of vaccines for the treatment or prevention of viral diseases such as AIDS where an antibody response may in fact enhance infectivity of the causative agent. Identification of such peptides is accomplished by injecting a candidate into an immunocompetent animal (e.g., mice) to identify those peptides that fail to generate a significant antibody response to the native protein to whose sequence the peptides correspond in part. For example, in the case of HIV, one would desire to test for the production of antibodies having reactivity against gp120, gp41 or core proteins, etc.

Of course, as mentioned above, the invention also concerns the identification of compounds capable of eliciting both a T cell response and a B cell response, in that this latter group will serve to induce protective antibody-based immunity in the immunized host.

CTL active compositions of the present invention prime T cells in a way that, when the infecting virus appears at a later date, memory T cells are activated to result in a cell-mediated immune response that destroys target cells that have the corresponding target protein or a portion thereof on their cell surfaces, and thereby the virus.

Thus, the present invention ultimately involves the preparation of CTL vaccines. Peptide multimers may find particular advantages in the preparation of CTL vaccines in accordance herewith. Preferred multimers are formed of surfactant-like micelles and polymers. In addition to the amino-terminal lysyl residue, the spacer peptide can contain one to about five additional residues. Substantially any amino acid residue can be utilized so long as it does not interfere with the T cell immunizing capacity of an aqueous composition containing the multimer or with the capacity of the di-amide reaction product to form surfactant-like micelles in an aqueous composition. One to about three glycyl residues per spacer peptide are preferred.

The before-described peptide and the amino-terminal lysyl residue-containing peptide spacer are peptide-bonded together, and can thus be viewed as a composite polypeptide. The useful diamide is thus a reaction product of the alpha- and epsilon-amino groups of the amino-terminal lysyl residue and two moles per composite polypeptide of the $C_{12}$–$C_{18}$ fatty acid. The composite polypeptide can thus be prepared as a single sequence and amidified before or after removal from the resin, where solid phase synthesis is used, by conventional techniques.

The phrase "surfactant-like micelle" is used herein to emphasize that, in an aqueous composition, the di-amidolysyl composite polypeptide appears to form micelles similar to those formed by surfactants and to distinguish such multimers from submicroscopic structural units of protoplasm built up from polymeric molecules that are also sometimes referred to as micelles. The word "micelle" is also sometimes used herein, and when so used has the same meaning as surfactant-like micelle.

Another multimer form of a previously described peptide is a polymer having a plurality of peptide repeating units. In this case, a peptide containing two terminal cysteines as part of its natural sequence can be selected and synthesized. A peptide lacking such cysteines can be modified by the addition of one or two extra cysteines to the N- and C-terminal ends, respectively. The presence of two cysteines per peptide permits polymerization of the subunit peptide by air oxidation to form oxidized cysteine(cystine)-linked polymers and/or cyclic peptides. Such multimers enhance immune recognition of the peptide without the need of a carrier.

The lysine-terminated spacer peptide can contain one to about five amino acid residues in addition to the lysyl residue, and the one or two added terminal cysteine residues are not included in counting the length of a peptide of the present invention. A peptide containing terminal cysteine residues is referred to as a di-cysteine-terminated peptide or more simply, a di-Cys peptide. Details for preparing polymers containing di-Cys peptide repeating units are provided hereinafter.

An aqueous composition (inoculum) of the present invention comprises an immunologically effective amount of a peptide or peptides, whether in multimeric form or not, dissolved or dispersed in a pharmaceutically acceptable aqueous medium. Such compositions are also referred to as inocula.

The phrase "pharmaceutically acceptable" refers to molecular entities and compositions that do not produce an allergic or similar untoward reaction when administered to a human.

The preparation of an aqueous composition that contains an immunizing molecule such as a peptide or multimer as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A peptide, e.g., a peptide multimer, can be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Upon vaccine formulation, it is administered in a manner compatible with the dosage formulation, and in such amount as is immunologically effective. By "immunologically effective amount" is meant an amount of composition is used that contains an amount of a peptide multimer sufficient to induce an effective CTL response in the host animal (mammal) such as by the induction of specifically targeted cytotoxic T cells. The presence of such cytotoxic T cells is assayed as discussed hereinafter.

In the context of a vaccine, the quantity of peptide and volume of composition to be administered depends on the host animal to be immunized, the capacity of the host animal's immune system to activate T cells, and the degree of protection desired. Precise amounts of active peptide multimer required to be administered depend on the judgment of the practitioner and are peculiar to each individual. However, suitable dosage ranges are of the order of about 10 micrograms ($\mu$g) to about 500 milligrams (mg), preferably about 50 $\mu$g to about 1 mg, and more preferably about 100 $\mu$g of active ingredient peptide multimer per individual. A minimal volume of a composition required to disperse the immunizing amount of peptide multimer is typically utilized. Suitable regimes for initial administration and booster shots are also variable, but are typified by an initial administration followed in one or two week intervals by a subsequent injection or other administration.

A composition can also include an adjuvant as part of the excipient. Adjuvants such as complete Freund's adjuvant (CFA), incomplete Freund's adjuvant (IFA) for use in laboratory host mammals are well known in the art, and are used illustratively herein. Pharmaceutically acceptable adjuvants such as alum can also be used.

EXAMPLE 1—Preparation of Peptides, Peptide Polymers and Peptide Micelles

Synthetic peptides of 7 to about 30 amino acid residues in length were prepared corresponding to the selected conserved domains of the core and gp160 (gp120 and gp41) molecules using the solid-phase technique of Merrifield (1963) using a modified Vega 250 automated peptide synthesizer or by the "bag" method described in Houghten (1985). In either case, removal of the t-butyloxycarbonyl (t-BOC) amino acid blocking groups and the hydrolysis of the peptide from the resin were carried accomplished by hydrofluoric acid (HF) treatment at 0° C. for one hour. The peptide-containing mixture was then extracted with diethyl ether to remove non-peptide organic compounds and the synthesized peptides were extracted from the resin with 25% acetic acid (w/v).

Nineteen (19) synthetic peptides have been prepared that correspond to conserved domains of the gp120 molecule and the gp41 molecule by this procedure, and are listed in TABLE 1. The synthesized peptides correspond to designated conserved domains (regions) of gp160 in HIV as shown.

TABLE 1

AMINO ACID SEQUENCE OF SYNTHETIC PEPTIDES

| PEPTIDE # | AMINO ACID SEQUENCE[1] | LOCATION IN HIV[2] ENVELOPE |
|---|---|---|
| 103 | $^{39}$EQLWVTVYYGVPV$^{51}$ | GP160-CR-1 |
| 104 | $^{45}$VYYGVPVWKEA$^{55}$ | GP160-CR-1 |
| 105 | $^{48}$GVPVWKEATTLFC$^{61}$ | GP160-CR-1 |
| 106 | $^{72}$AHKVWATHACV$^{82}$ | GP160-CR-1 |
| 107 | $^{81}$CVPTNPVPQEVV$^{92}$ | GP160-CR-1 |
| 108 | $^{92}$VLENVTENFNM$^{102}$ | GP160-CR-1 |
| 109 | $^{105}$NNMVEQMHEDI$^{116}$ | GP160-CR-1 |
| 110 | $^{109}$EQMHEDIISLWDQ$^{121}$ | GP160-CR-1 |
| 111 | $^{118}$LWDQSLKPCVKLT$^{130}$ | GP160-CR-1 |
| 112 | $^{121}$SLKPCVKLTPLC$^{133}$ | GP160-CR-1 |
| 113 | $^{204}$SVITQACSKVSFE$^{216}$ | GP160-CR-2 |
| 114 | $^{215}$FEPIPIHYCAFPGF$^{228}$ | GP160-CR-2 |
| 115 | $^{236}$KKFNGTGPCTN$^{246}$ | GP160-CR-2 |
| 116 | $^{240}$GTGPCTNVSTVQC$^{252}$ | GP160-CR-2 |
| 117 | $^{250}$VQCTHGIRPVVSTQ$^{263}$ | GP160-CR-2 |
| 61 | $^{586}$YLRDQQLLGIWGC$^{598}$ | GP160-CR-5 |
| 63 | $^{519}$FLGFLGAAGSTMGAASL-TLTVQANQ$^{543}$ | GP160-CR-5 |
| 65 | $^{417}$CRIKQIINMWQGVGKAMYA$^{435}$ | GP160-CR-3 |
| 67 | $^{417}$CRIKQIINMWQGVGKAM-YAPPIGGQIRC$^{444}$ | GP160-CR-3 |

[1]The N- and C-terminal amino acid residues of each peptide are numbered as to their position in the gp160 amino acid residue sequence according to Modrow et al. Virol., 61:570 (1987). A dash (-) indicates that the sequence continues on the next line.
[2]CR = Conserved Region Two types of high molecular weight (multimeric) forms of the peptides listed in TABLE 1 were prepared. The principal form of multimer was a di-cysteine (di-Cys terminated) polymer in which a plurality of peptides were linked end-to-end by disulfide bonds. These di-cysteine polymers were produced by adding cysteine residues to the termini of each peptide during synthesis. The di-cysteine-terminated (di-Cys) peptides were then dissolved (10 mg/ml) in ammonium bicarbonate (0.1M) at room temperature (~25° C.) and stirred for about 16 hours to effect oxidation of the sulfhydryl groups to produce polymer forms of the peptides. The peptide solution was freeze-dried and analysed by HPLC to confirm the presence of polymer forms of the peptide.

The second type of high molecular weight form produced was a surfactant-like micelle formed by linkage of an amino-terminal lysine-containing spacer peptide (Lys-Gly-Gly-) to the peptide sequence to form a composite polypeptide, and then coupling a $C_{12}$–$C_{18}$ fatty acid, such as palmitic acid, to both the alpha and epsilon amino groups, as in Hopp (1984). The $C_{12}$–$C_{18}$ fatty acid-containing peptides produced are then extracted in 95% acetic acid and utilized to form large micelles in the aqueous composition that exhibit increased immunogenicity relative to the peptides.

Di-Cys polymer multimers of all of the peptides listed in TABLE 1 were prepared. Aqueous peptide micelle multimers have been prepared of peptides designated 61, 63, 65 and 67, and are designated as peptides 62, 64, 66 and 68, respectively. Peptides designated 103 through 117 were utilized only in their di-Cys polymer multimeric forms.

The high molecular weight, multimeric forms produced correspond to multiple copies of specific regions of gp120 and gp41 in HIV. For ease of designation, the multimer forms will be designated by the peptide number from which it is composed—that is, peptide 61 refers to the di-Cys multimeric (polymeric) form of peptide 61 and peptide 66 refers to the aqueous micelle form of peptide 65, whereas peptide 103–117 refers to a polymeric multimer.

Peptides 65 and 66 correspond to the region of gp120 that binds to the cell surface T4 receptor. Peptides 61 and 62 correspond to a region near the amino-terminal portion of gp14 that represents a major immunodominant epitope seen by AIDS patients' sera.

EXAMPLE 2—Anti-Peptide Antibody Response

Aqueous compositions of the multimers; i.e., the di-Cys peptide polymers and micelles produced in EXAMPLE 1 were assayed for their ability, or lack of ability to elicit an anti-peptide antibody response in BALB/c mice, an immunocompetent mouse strain.

Groups of BALB/C mice (6–8-week-old females, 3 to 5 mice/group, Charles River Laboratories) were immunized by subcutaneous (s.c.) or intraperitoneal (i.p.) injection of a peptide multimer (100 μg/injection) in complete Freund's adjuvant (CFA) (1:1 ratio). Booster injections (50 μg of peptide multimer) in incomplete Freund's adjuvant (IFA) (1:1) were given at 6 and 10 weeks after the initial immunization. Each mouse was bled from its retro-orbital plexus at two-week intervals and the serum was pooled for individual mice in each group.

An ELISA assay was performed on each serum to detect the presence of anti-peptide antibodies utilizing peroxidase-conjugated goat anti-mouse IgG (Boehringer Mannheim Biochemicals, Indianapolis, Ind.) as the second antibody. Preliminary results for peptides 61–68 are shown in TABLE 2, whereas further refined results for peptides 61, 63, 65, 67 and 103–117 are shown in TABLE 3. It was found that the high molecular weight forms of peptides 65, 66, 67, 68, 105 to 110, 112, 114, 115 and 117 elicited high antibody titers, whereas peptides 61, 62, 63, 64, 103, 104, 111, 113 and 116 produced very low to negligible amounts of anti-peptide antibodies. Similar results were obtained for antibody responses in B6C3 F1 mice (Charles River Laboratories), another immunocompetent strain.

Some of the sera were further assayed for antibody response (reactivity) with native gp160, and the results, shown in TABLE 4, demonstrate that these peptides do not represent B cell epitopes since there was no immunoreaction with native gp160.

TABLE 2

ANTIBODY RESPONSE OF VARIOUS PEPTIDES IN BALB/c MICE
ELISA Titer in Bleed #

| Peptide # | Pre-Immuno | 1 | 2 | 3 | 4 | 5 | 6 | 7 | 8 |
|---|---|---|---|---|---|---|---|---|---|
| 61 | 1:40 | 1:400 | 1:100 | 1:100 | 1:100 | 1:100 | 1:400 | 1:200 | 1:400 |
| 62 | 1:20 | 1:100 | 1:100 | 1:100 | 1:100 | 1:100 | 1:200 | 1:100 | 1:100 |
| 63 | 1:40 | 1:80 | 1:20 | 1:40 | 1:320 | 1:80 | 1:80 | 1:320 | 1:5120 |
| 64 | 1:20 | 1:40 | 1:40 | 1:80 | 1:40 | 1:40 | 1:40 | 1:40 | 1:40 |
| 65 | 1:40 | 1:80 | 1:800 | $1:1 \times 10^4$ | $1:5 \times 10^4$ | $1:5 \times 10^4$ | $1:2 \times 10^5$ | $1:2 \times 10^5$ | $1:2 \times 10^5$ |
| 66 | 1:40 | 1:160 | $1:6 \times 10^3$ | $1:1 \times 10^5$ | $1:1 \times 10^5$ | $1:1 \times 10^5$ | $1:2 \times 10^4$ | $1:5 \times 10^4$ | $1:5 \times 10^4$ |
| 67 | 1:40 | 1:160 | $1:3 \times 10^3$ | $1:2 \times 10^4$ | $1:2 \times 10^4$ | $1:1 \times 10^5$ | $1:8 \times 10^5$ | $1:1 \times 10^5$ | $1:2 \times 10^5$ |
| 68 | 1:80 | 1:1600 | $1:1 \times 10^4$ | $1:1 \times 10^4$ | $1:1 \times 10^5$ | $1:1 \times 10^5$ | $1:4 \times 10^5$ | $1:4 \times 10^5$ | $1:4 \times 10^5$ |

TABLE 3

ANTIBODY RESPONSE OF VARIOUS PEPTIDES IN BALB/C MICE

| PEPTIDE | ELISA TITER |
|---|---|
| #61 AA 586–598 | 1:400 |
| #63 AA 519–543 | 1:5120 |
| #65 AA 417–435 | $1:2 \times 10^5$ |
| #67 AA 417–444 | $1:8 \times 10^5$ |
| #103 AA 39–51 | 1:640 |
| #104 AA 45–55 | 1:2000 |
| #105 AA 48–61 | 1:5000 |
| #106 AA 72–82 | $1:4 \times 10^5$ |
| #107 AA 81–92 | $1:1 \times 10^5$ |
| #108 AA 92–102 | $1:1 \times 10^5$ |
| #109 AA 105–116 | $1:8 \times 10^5$ |
| #110 AA 109–121 | $1:6 \times 10^6$ |
| #111 AA 118–130 | 1:80 |
| #112 AA 121–133 | $1:1 \times 10^5$ |
| #113 AA 204–216 | 1:640 |
| #114 AA 215–228 | $1:1 \times 10^6$ |
| #115 AA 236–246 | $1:4 \times 10^5$ |
| #116 AA 240–252 | 1:640 |
| #117 AA 250–263 | $1:8 \times 10^6$ |

TABLE 4

T AND B CELL RESPONSES IN MICE TO HIV
ENVELOPE GP160 DERIVED SYNTHETIC PEPTIDE IMMUNOGENS

| | In Vitro Proliferation of PLN Cells from* | | | | Antipeptide Antibody Reactivity to** | |
|---|---|---|---|---|---|---|
| | $B_6C_3F_1$ | | $A \cdot SWxBalb/c\ F_1$ | | | |
| Peptide Immunogen | Analogous Peptide | GP 160 | Analogous Peptide | GP 160 | Analogous Peptide | GP 160 |
| 61 | ++ | + | ++ | ++ | − | − |
| 63 | ++ | ++ | ++ | ++ | ± | − |
| 65 | ++ | + | ++++ | ++ | ++ | − |
| 67 | ++ | − | ++++ | ++ | +++ | − |
| 103 | + | + | +++ | + | − | − |
| 104 | ++++ | ++ | +++ | + | ± | − |
| 105 | ++++ | +++ | + | − | ± | − |
| 106 | +++ | + | ++++ | + | ++ | − |
| 107 | ++ | ++ | + | + | + | − |
| 108 | + | + | + | − | + | − |
| 109 | ++ | ± | ± | + | +++ | − |
| 110 | ++ | − | ++ | + | ++++ | − |
| 111 | + | ++ | ± | − | − | − |
| 112 | + | + | + | + | + | − |
| 113 | ++ | + | ++ | + | − | − |
| 114 | ++ | − | ++ | + | ++++ | − |
| 115 | ++ | + | ◊ND | ND | ++ | − |

TABLE 4-continued

T AND B CELL RESPONSES IN MICE TO HIV ENVELOPE GP160 DERIVED SYNTHETIC PEPTIDE IMMUNOGENS

| | In Vitro Proliferation of PLN Cells from* | | | | Antipeptide Antibody | |
| --- | --- | --- | --- | --- | --- | --- |
| | $B_6C_3F_1$ | | A·SWxBalb/c $F_1$ | | Reactivity to** | |
| Peptide Immunogen | Analogous Peptide | GP 160 | Analgous Peptide | GP 160 | Analogous Peptide | GP 160 |
| 116 | ++ | − | ND | ND | − | − |
| 117 | +++ | − | ND | ND | ++++ | − |

*cpm values are corrected and categorized according to unrelated antigen response in vitro.
**Antibody raised in Balb/C mice, reactivity measured by ELISA and categorize according to the end point.
◊Not determined.

EXAMPLE 3—T Cell Responses

The high molecular weight, multimeric di-Cys peptide polymeric forms of the peptides described in EXAMPLE 1 were assayed for their elicitation of a T cell proliferative response as in Millich et al. (1985).

Mice (3 or 5 mice/group) were injected in the right hind footpad with a 1:1 mixture of peptide polymer (100 µg/injection) and CFA. Peptides 61, 63, 65 and 67 were injected into B6C3 F1 mice (H-$2^{kxb}$, Charles River Laboratories) and A.SWXBALB/C F1 mice (H-$2^{sxd}$, Jackson Labs, Bar Harbor, Me.). Draining popliteal lymph node (PLN) cells were harvested after ten (10) days, and cultured ($2 \times 10^5$ cells/well) in 96-well microtiter plates in 0.2 ml of Click's medium (Click et al., 1972) containing various concentrations of synthetic peptide, gp160, an unrelated proteinaceous material or medium alone, for 96 hours at 37° C. in a humidified atmosphere of 5% $CO_2$. During the final 16–18 hours of culturing, $^3$H-thymidine ($^3$H-TdR) (1 µCi/well, 6–7 Ci/mmole, ICN Radiochemicals) was added. The cells were harvested onto filter strips and $^3$H-TdR incorporation was monitored. The data are presented in FIGS. 1, 2, 3, 4 and 5.

FIG. 1 illustrates the results for peptides 61, 63, 65, 67 in BALB/C mice, and those results are expressed as a stimulation index (SI) representing the fold increase in radioactivity counts in the presence of antigen compared to background values where no antigen was added. The SI values with the different peptides were compared to that obtained with tuberculin purified protein derivative (PPD) as a positive control antigen.

FIGS. 2–5 illustrate the peptide-specific $^3$H-TdR incorporation for T cell responses (delta cpm) in mice with differing major histocompatibility (MHC) haplotypes, B6C3 F1 (C57B1/6x$C^3$H/HcJ) mice (FIGS. 2 and 4) and (A.SWxBALB/c) F1 mice (FIGS. 3 and 5), for all of the synthetic peptides. The $^3$H-TdR incorporation values represent the difference between the radioactivity values obtained in wells containing antigen and in control wells without added antigen. The non-specific proliferation of PLN cells was determined by including an unrelated peptide in the assays, shown as a horizontal bar for each peptide.

All of the assayed peptides exhibited good T cell proliferative responses in B6C3 F1 mice, whereas all of the assayed peptides, except peptides 105, 107, 109 and 111, exhibited good T cell proliferative responses in A-SWxBALB/c F1 mice.

It was demonstrated by the results above and those described in EXAMPLE 2 that peptides 61, 63, 103, 104 and 113 do not stimulate anti-peptide antibody production but are very good immunogens, in their disulfide (di-Cys) polymeric form, for eliciting a strong T cell response directed against both the corresponding peptide and the native HIV envelope protein gp160.

Figure 6A:
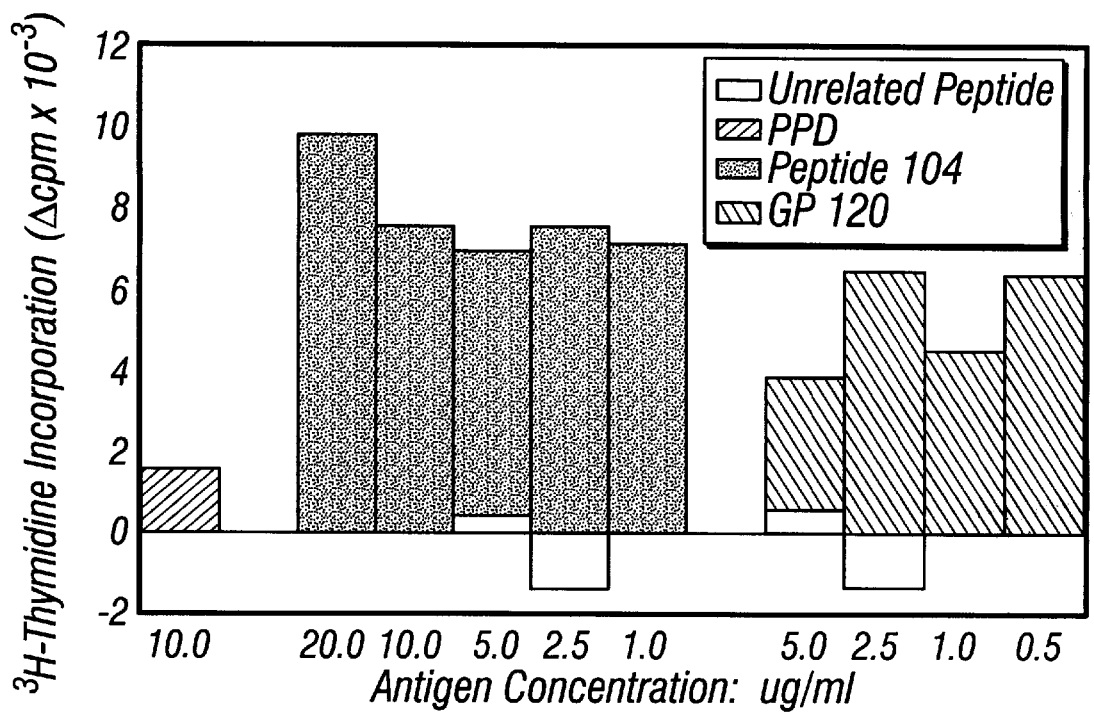
Figure 6B:
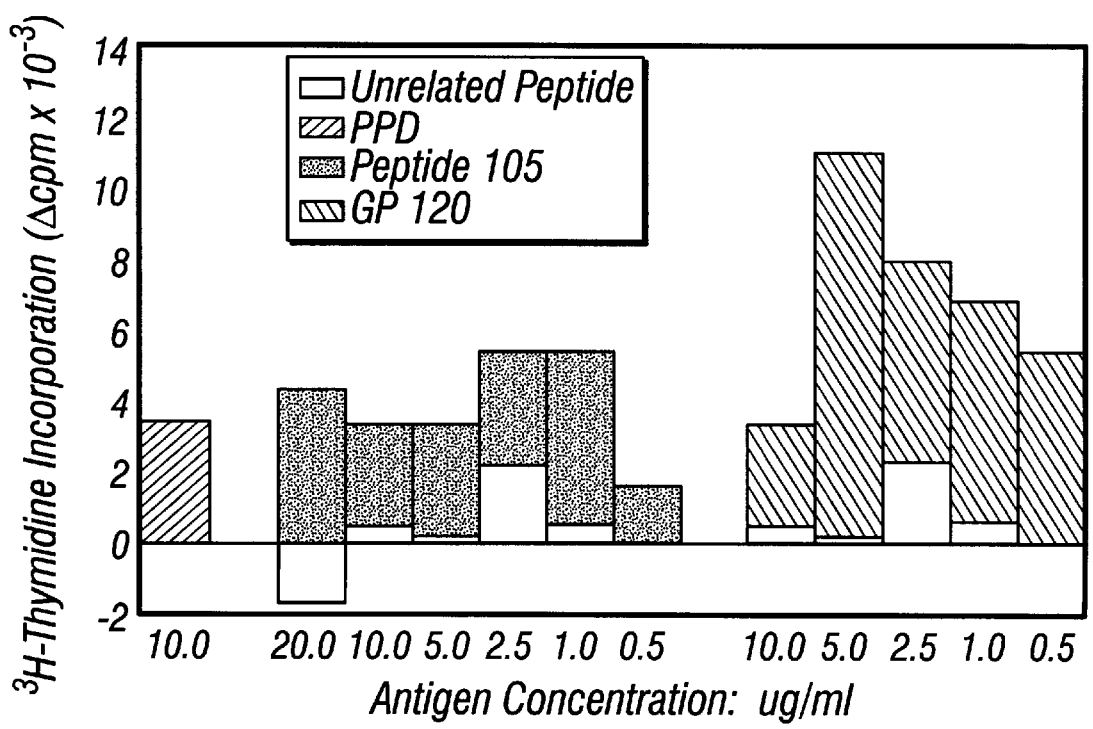
Figure 7A:
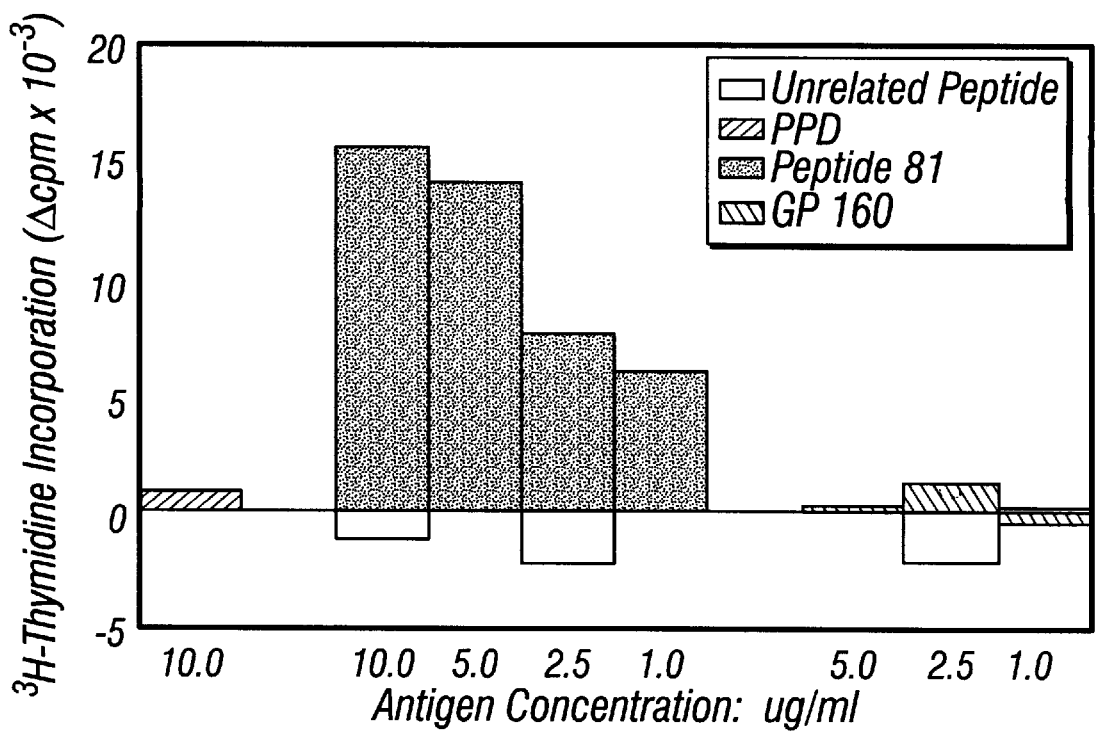
FIG. 7A. PLN cell proliferation from B6C3 F1 mice using various concentrations of gp160 and peptide multimer polymers prepared from peptide 61 as antigens, with PPD, and an unrelated peptide as controls.
Figure 7B:
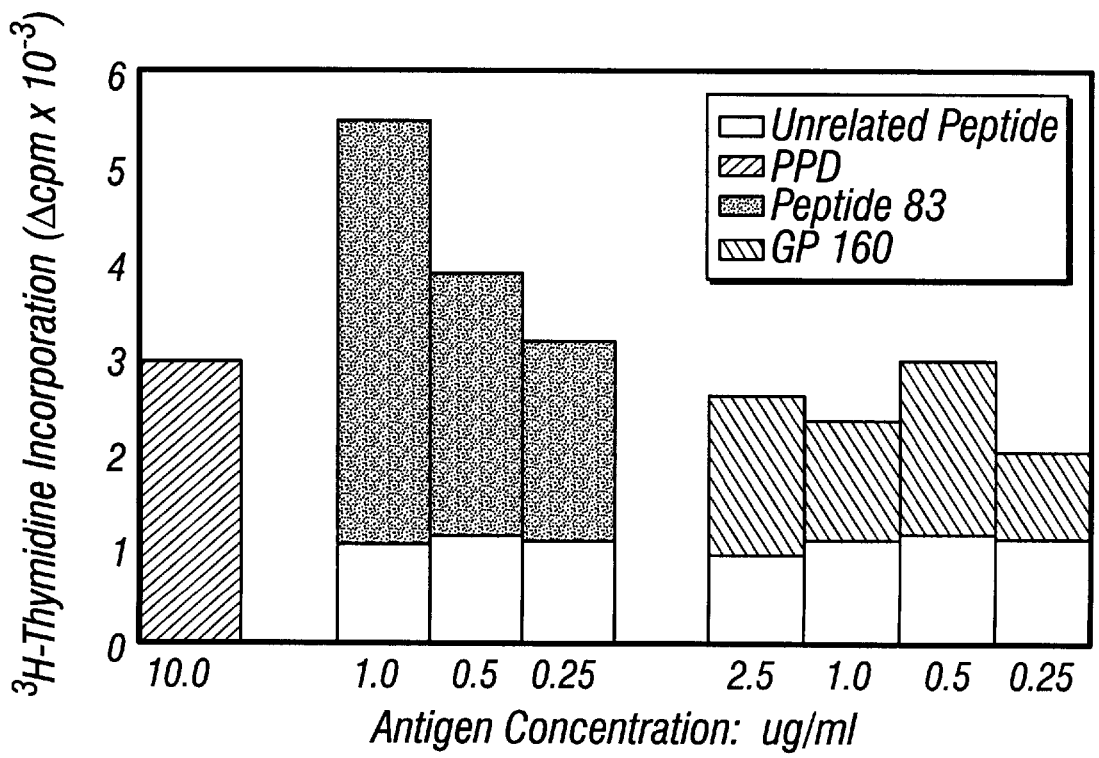
FIG. 7B. Same as FIG. 7A, except the peptide multimer polymers prepared from peptide 63 as antigen.
Figure 8A:
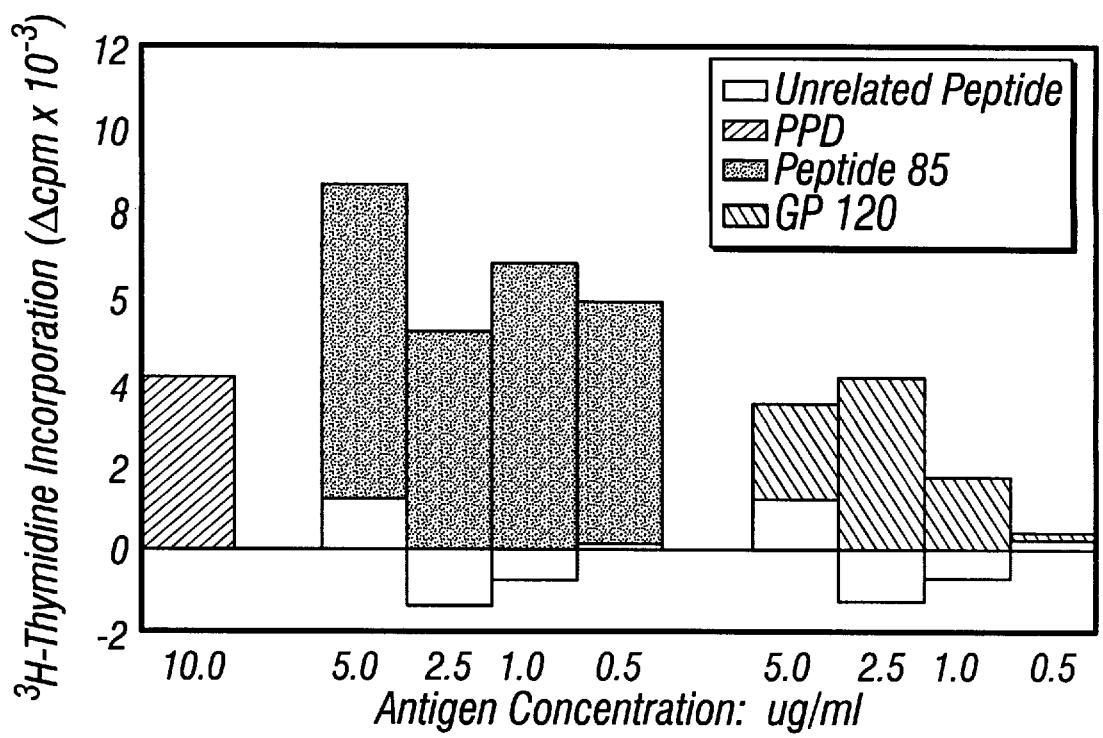
FIG. 8A. PLN cell proliferation from B6C3 F1 mice using various concentrations of gp120 and peptide multimer polymers prepared from peptide 65 as antigen, with PPD and an unrelated peptide as controls.
Figure 8B:
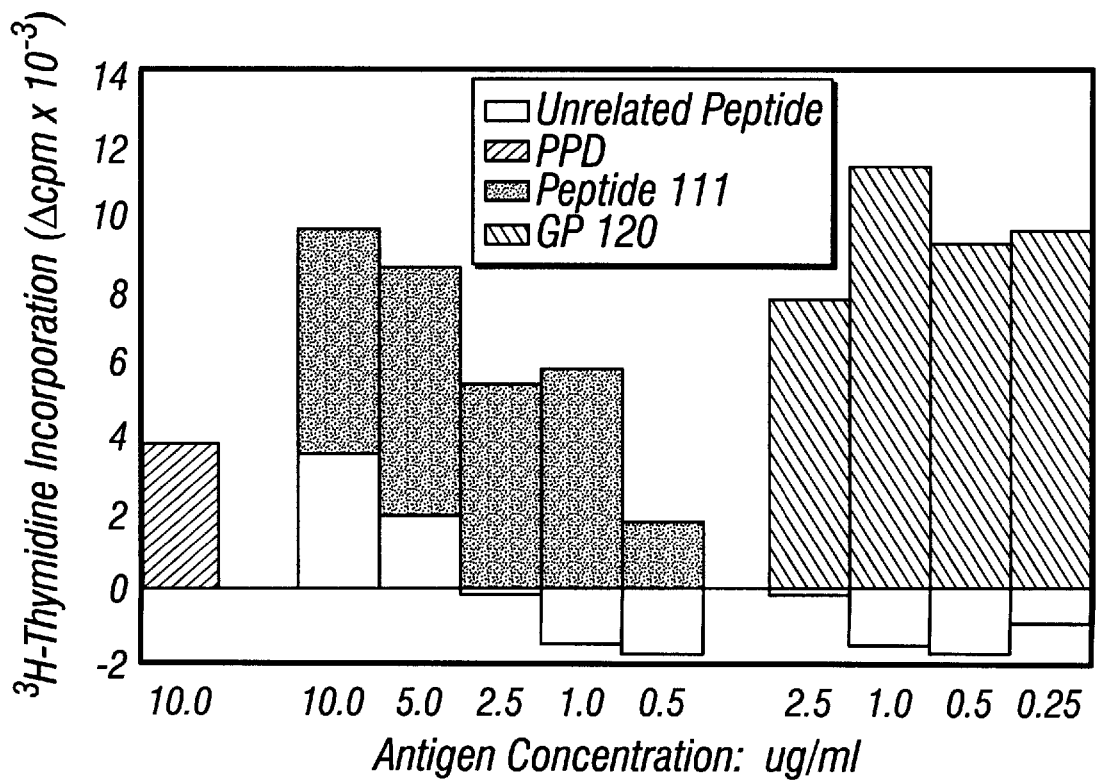
FIG. 8B. Same as FIG. 8A, except the peptide multimer polymers prepared from peptide 111 as antigen.

T cell proliferation measured by $^3$H-TdR incorporation, was also similarly assayed as a function of the T cell antigen concentration, using various amounts of native gp120 or gp160 as one control, and PPD as another control. PLN from B6C3 F1 mice were used in these studies. The results for peptides 104 and 105 versus gp120 are shown in FIGS. 6A and 6B, respectively; those for peptides 61 and 63 versus gp160 are shown in FIGS. 7A and 7B, respectively; and those for peptides 65 and 111 versus gp120 are shown in FIGS. 8A and 8B, respectively.

EXAMPLE 4—Induction of HIV-Specific Cytotoxic T Lymphocytes

Groups of 3 to 5 syngeneic female mice (6 to 8 weeks of age) are immunized by intradermal injection in an appropriate site with an aqueous composition containing an immunizing (CTL-stimulating) amount of peptide either as monomer or as the before-discussed multimers in CFA (1:1). Ten (10) days after immunization, draining PLN cells and spleen lymphocytes are obtained and restimulated in vitro by culturing for six (6) days with irradiated syngeneic normal spleen cells that were pre-treated with the same synthetic peptide as immunogen.

The presence of cytotoxic T lymphocytes (CTL) is determined by a 4-hour $^{51}$Cr release assay as follows. The PLN cells are maintained for five days at 37° C. in Clicks medium containing 10% fetal calf serum (FCS) together with irradiated syngeneic normal spleen cells that were pre-treated with the approriate test peptide. These cells are designated as the effector cells, and express H-$2^d$ MHC class I antigen.

Target cells (phytohemagglutinin-stimulated (PHA) blasts of syngeneic mouse spleen cells or P815 mouse cells expressing a corresponding HIV protein) are washed three times with serum-free RPMI 1640 medium and then admixed, contacted and maintained (incubated) at 37° C. for about 1.5 to about 2 hours together with 250 µCi of sodium chromate (specific activity 200–400 Ci/g of $^{51}$Cr, New England Nuclear, Boston, Mass.). The target cells are subsequently washed with RPMI 1640 medium containing 10% FCS, and resuspended in RPMI 1640 with 10% FCS and different concentrations of peptide. These cells are then washed 3 times with RPMI containing 10% FCS and resuspended at $5 \times 10^4$ cells/ml. A 100 µl aliquot of each cell suspension is added to a well of a 96-well-U-bottom microtiter plate.

A 100 μl aliquot of the appropriate effector cell suspension (5×10⁶ cells/ml) is added to each well and a twofold serial dilution made to obtain different effector-to-target cell (E:T) ratios. Control wells receive 0.1 ml of RPMI medium with 10% FCS alone in the absence of effector cells to obtain a value for spontaneous $^{51}$Cr release, and receive 0.1 ml of 5% Triton X-100 detergent to obtain a value for maximum $^{51}$Cr release.

The plates are incubated at 37° C. for about 4 hours, following which 100 μl of supernatant from each well is monitored in a gamma counter to determine $^{51}$Cr release. The percent cytotoxicity is calculated as $$\frac{(\text{Effector Cell} - \text{Stimulated Release}) - (\text{Spontaneous Release})}{\text{Maximum Release} - \text{Spontaneous Release}} \times 100$$

EXAMPLE 5—Rapid assay of HIV-specific CTLs Induced by an Immunodominant peptide.

A peptide with the sequence RIQRGPGRAFVTIGK (herein referred to as R15K), from the HIV gp160 immunodominant V3-loop has previously been identified as a CTL immunodominant epitope in H-2$^d$ mice (Takahashi et al., 1988). In the original studies CTLs, induced in vivo by infecting Balb/c mice with recombinant vaccinia virus expressing HIV env proteins, were shown to lyse syngeneic target cells pre-incubated with R15K. Unfortunately, to date, immunizing mice with free R15K peptide has been unsuccessful in inducing CTLs (Berzofsky, 1991).

Accordingly, the present inventors sought to examine the induction of CD8⁺ HIV R15K-specific CTLs in 6–8 week old Balb/c mice by employing differing sites of inoculation, differing forms of the peptide, and recovering the effector cells from different tissue origins. It was observed that draining popliteal lymph nodes (PLN) of mice immunized in the hind-foot pad with 100 μg of the R15K peptide (in a 1:1 emulsion with CFA) were the best source of CTL effectors against irradiated (3300 rads) syngeneic target cells preincubated with monomeric R15K (40 μg/ml for 2 h at 37° C.). This has particular importance and physiological significance because human lymph nodes have been described as the primary site of HIV replication (Kaneshima et al., 1991; Fauci 1991). An important aspect of this immunization protocol is that CTLs could be recovered by mild homogenization from PLN surgically removed after only 10 days.

Figure 9:
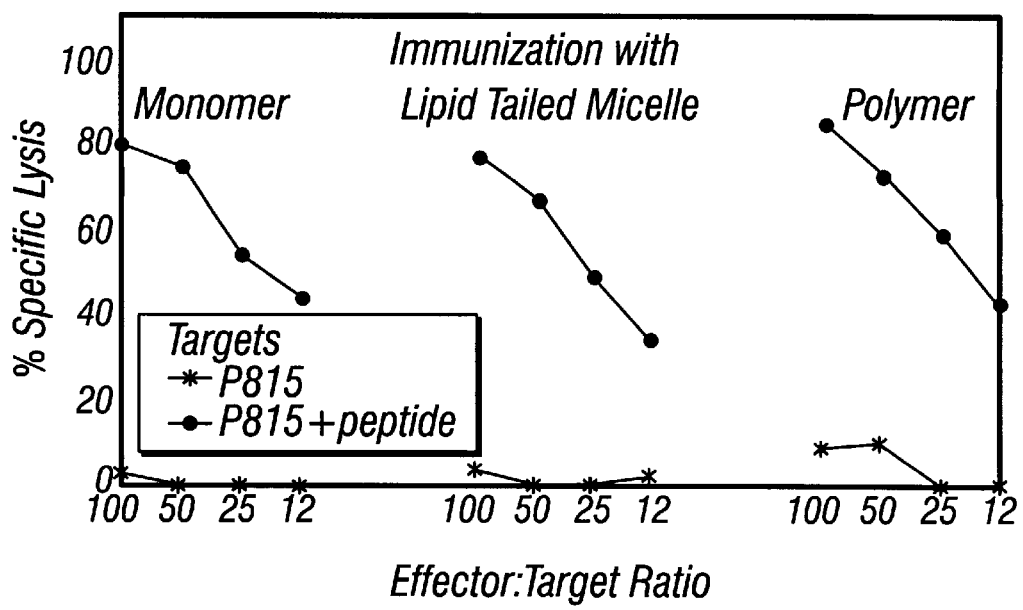
FIG. 9. CTL activity of popliteal lymph node (PLN) cells from Balb/c mice after immunization with HIV env V3-loop R15K peptide (aa 315–329) in three forms. A, linear monomer; B, di-sulphide-linked polymers formed by cysteine residues added at both the N- and C- termini; C, lipid-tailed micelles formed by conjugation to a dipalmityl-lysine-glycine-glycine at the N-terminus (Hopp, 1984; Sastry et al., 1991). Balb/c mice (6–8 weeks of age) were immunized in the hind-foot pad with the peptide (100 μg in a 1:1 emulsion with CFA). After 10 days, cells obtained from the PLN were re-stimulated in vitro for 5 days with irradiated (3300 rads) syngeneic mouse spleen cells that had been pre-treated with the monomeric form of the peptide (40 μg/ml) for 2 h at 37° C. The cell mixtures were maintained in 5–10 ml of Click's medium (Click et al., 1972) supplemented with 10% fetal calf serum (FCS) and 50 μM 2-mercaptoethanol, then washed three times with RPMI 1640 medium, 10% FCS. The CTL activity was determined by $^{51}$Cr-release assay (Platsoucas & Good, 1981) against syngeneic target cells (P815) with or without pre-treatment with the monomeric form of the peptide for 2 h at 37° C.

To determine the optimal form of the peptide for consistent induction of peptide-specific CTLs in vivo, the R15K peptide was prepared in three different configurations: a) linear monomer, b) disulphide-linked polymer formed by oxidation of cysteine residues added at both the N- and C-termini and c) micelles formed by conjugating the peptide to a dipalmityl-lysine-glycine-glycine at the N-terminus (Hopp, 1984; Sastry and Arlinghaus, 1991). It was found that a single immunization of Balb/c mice in the hind-foot pad with any of the above R15K forms in CFA consistently resulted in generation of CTLs which specifically lysed MHC-matched target cells (P815, H-2$^d$) pre-incubated with the peptide. Such responses were observed in 8 of 12 mice immunized with the monomeric form, in 13 of 13 mice immunized with the micelle form and 6 of 8 mice immunized with the disulfide polymer form of the peptide. Lysis of MHC-matched target cells without peptide pre-treatment (P815) was not observed. Representative results are shown in FIG. 9.

Figure 10A:
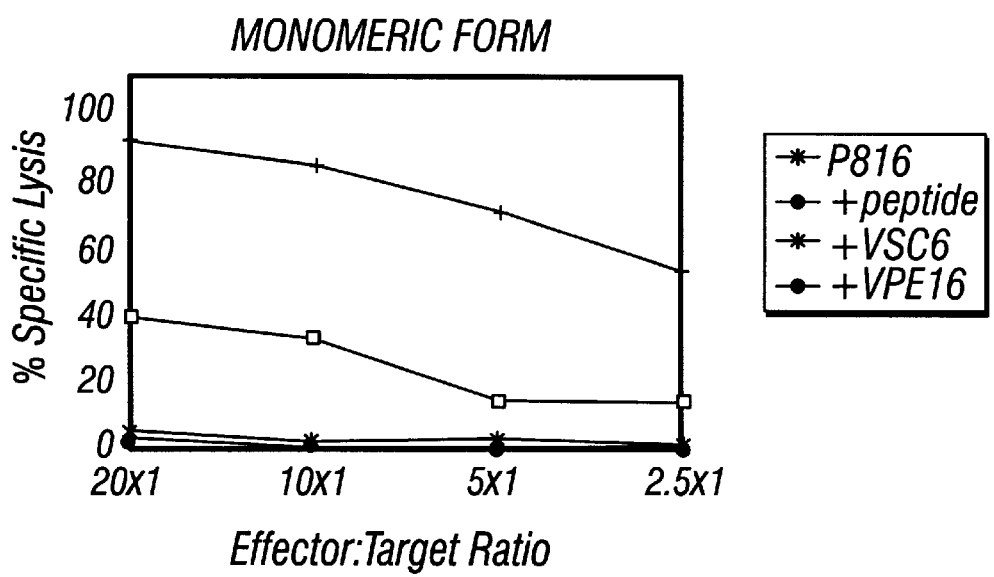
FIG. 10A. CTLs from Balb/c mice immunized in vivo with monomeric R15K-tpye peptides recognize MHC-matched target cells that were either pre-treated with peptide monomers (P815+peptide) or infected with recombinant vaccinia virus expressing the HIV IIIB envelope protein, gp160 (P815+VPE16). Immunization of mice and peptide pre-treatment of P815 target cells was carried out as in FIG. 9. 5×10$^6$ P815 target cells were infected with 5×10$^7$ plaque forming units of control (VSC8) or recombinant vaccinia virus expressing HIV envelope protein (VPE16) for 18–20 hours prior to labelling with 100 μCi of $^{51}$Cr (ICN Radiochemicals, Irvine, Calif.). The cytotoxic activity was determined by $^{51}$Cr-release assay (Platsoucas & Good, 1981).
Figure 10B:
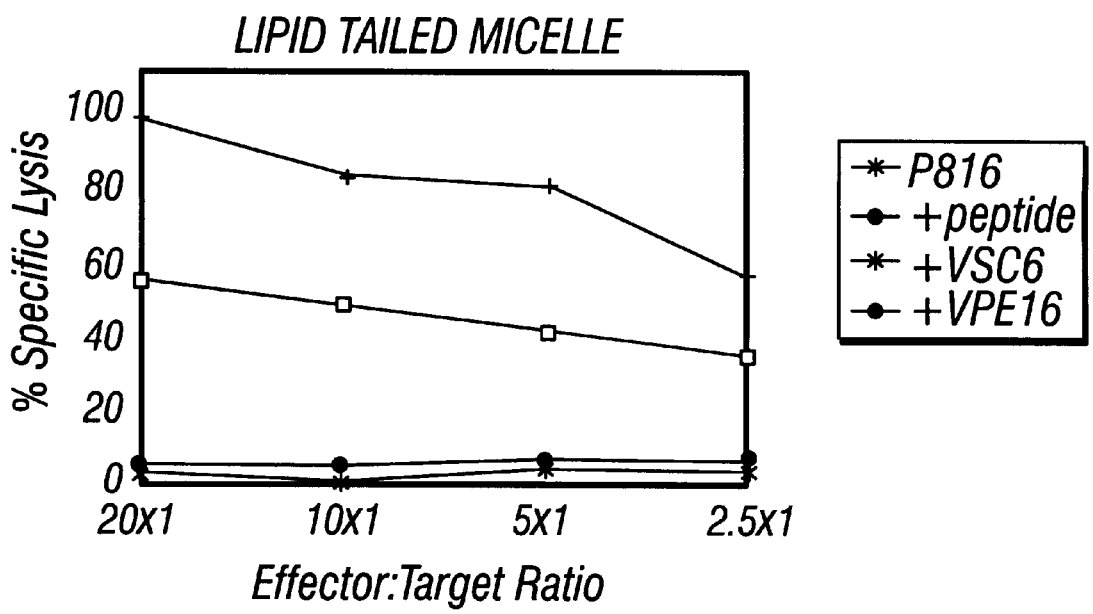
FIG. 10B. Same as FIG. 10A, except the peptide was in micelle form.
Figure 10C:
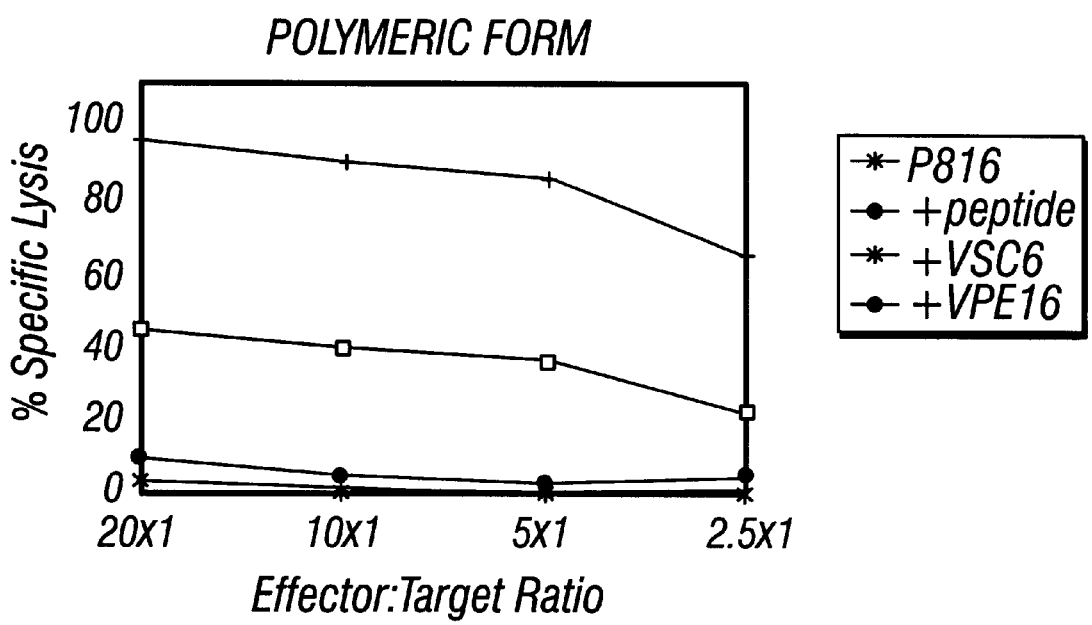
FIG. 10C. Same as FIG. 10A, except the peptide was in polymeric form.

The CTLs induced by all three forms of the peptide also specifically lysed P815 cells infected with a recombinant vaccinia virus expressing HIV gp160 (VPE16), but not cells infected with a control vaccinia virus (P815+VSC8) (FIG. 10). Western blotting with HIV antibody-positive human sera confirmed the presence of gp160 protein in VPE16-infected, but not in VSC8-infected P815 target cells. The peptide-induced CTLs in Balb/c mice were H-2 restricted. They lysed only peptide pre-treated H-2$^d$ target cells (P815) but not peptide-treated 3A9 target cell, which are expressing the H-2K haplotype (TABLE 5).

Representative results with CTLs generated in mice immunized with the micelle form of R15K peptide are shown in TABLE 5. Similar results were obtained with CTLs induced by injection of the monomeric and polymeric forms of the R15K peptide.

Figure 11A:
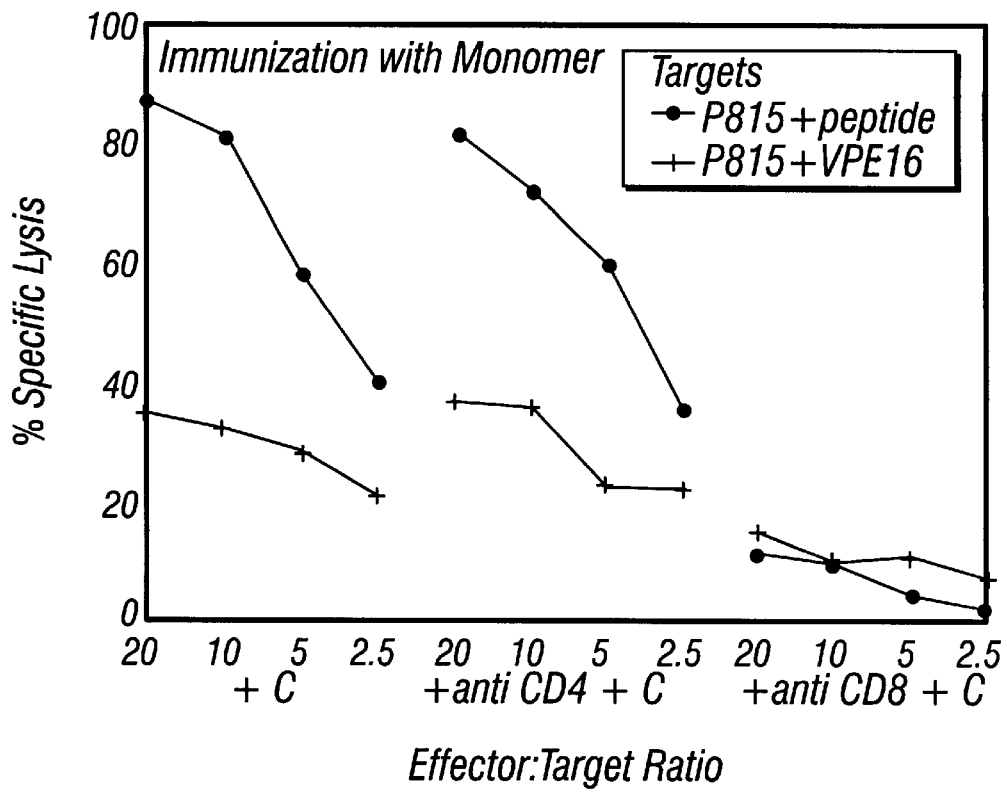
FIG. 11A. CTLs primed by in vivo immunization with the monomeric form of the HIV V3-loop R15K peptide are CD8-positive. Re-stimulated PLN cells (as in FIG. 9) were treated with complement along (+C) or with either anti-CD4 monoclonal antibody (clone GK-1.5) plus C (+ anti CD4-C) or anti-CD8 monoclonal antibody (clone 53–6.72) plus C (+anti CD8+C) as in (Platsoucas & Good, 1981). Resulting cells were then tested for their capacity to lyse MHC-matched target cells that were either pre-treated with the monomeric form of the peptide (P815+peptide) or infected with recombinant vaccinia virus expressing HIV IIIB envelope protein gp160 (P815+VPE16).
Figure 11B:
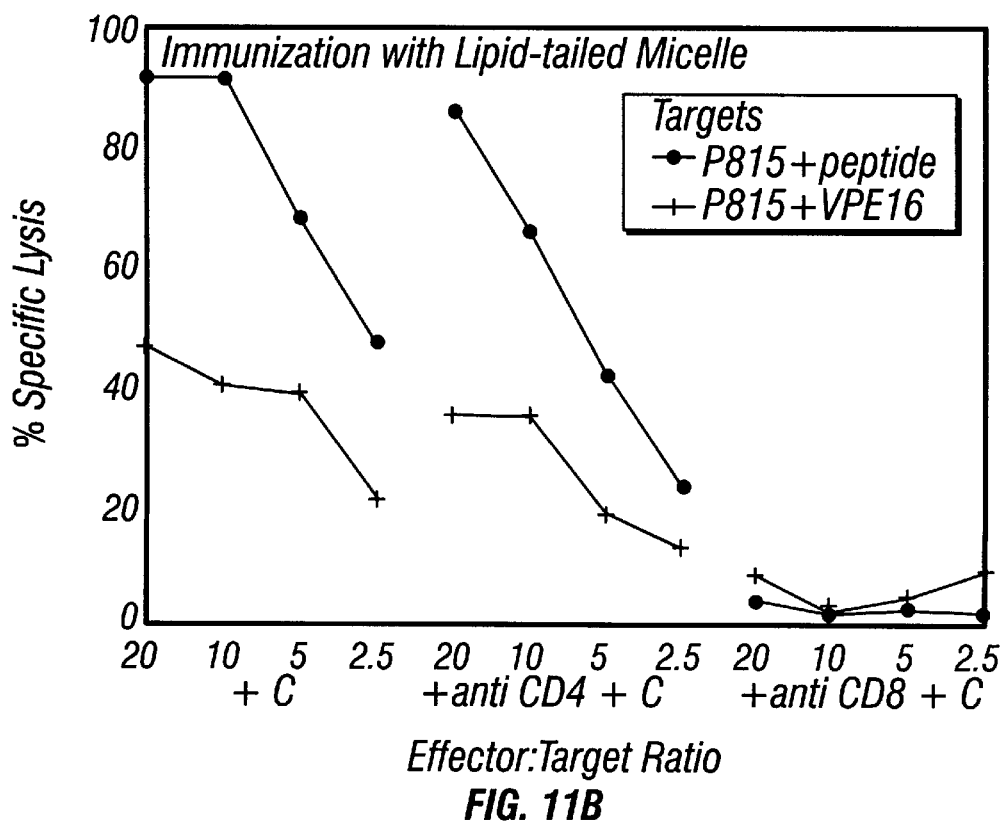
FIG. 11B. Same as FIG. 11A, except the peptide was in the lipid-tailed micelle form.

Experiments were performed to determine whether the virus-specific CTLs were CD8⁺ or CD4⁺. Treatment of the CTL effectors from mice immunized with monomeric peptide with anti-CD8 monoclonal antibodies (MAbs) and rabbit complement abolished the cytotoxicity against peptide treated, or env expressing, targets (FIG. 11A). In contrast, pre-treatment of effector cells with anti-CD4 MAbs plus complement, or complement alone, had no significant effect. Similar results were also obtained with CTLs generated in mice immunized with the peptide in micelle (FIG. 11B) and polymeric forms. The induction of CD8⁺ CTLs by R15K is consistent with the use of P815 target cells which express MHC class I, but not class II, gene products (Maryanski et al., 1985). MHC class I-restriction is commonly observed with CD8⁺ effector CTLs.

Since the CTL epitope studied in the present investigation is in the middle of an immunodominant B-cell active region of the HIV gp120, the B-cell activity of the R15K peptide was investigated. Either as monomer or lipid tailed micelle or after conjugation to KLH, this peptide failed to induce in mice a measurable titer of anti-peptide antibody. However, the mice immunized with peptide conjugated to KLH did make antibodies against KLH, showing that the mice are immunocompetent. Sera from mice immunized in the foot pad were also tested, when it was observed that no anti-peptide antibodies were formed.

TABLE 5

Peptide and target cell specificity of CTLs induced in Balb/c mice by the HIV env V3-loop R15K peptide

| Target Cells | % specific lysis at various E:T$^a$ ratios | | |
|---|---|---|---|
| | 100:1 | 50:1 | 25:1 |
| P815$^b$ | 7.2 | 0 | 0 |
| P815 + A84$^c$ | 76.7 | 67.2 | 65.9 |
| P815 + B106$^d$ | 4.2 | 0.6 | 0 |
| P815 + B105$^e$ | 6.7 | 0 | 0 |
| 3A9$^f$ | 7.0 | 0.6 | 0 |
| 3A9 + A84$^g$ | 10.0 | 8.0 | 0 |

$^a$= Effector to Target cell ratio
$^b$= MHC-matched target cells (H-2$^d$)
$^c$= H-2$^d$ cells pre-treated with HIV env V3-loop R15K peptide
$^d$= H-2$^d$ cells pre-treated with a Influenza virus peptide$^{24}$
$^e$= H-2$^d$ cells pre-treated with a Sendai virus peptide$^{26}$
$^f$= MHC-mis-matched target cells (H-2$^k$)
$^g$= H-2$^k$ target cells pre-treated with HIV env peptide V3-loop Despite the results presented immediately above, the location of R15K in a variable region (V3-loop) of HIV gp160 could be viewed as a reason for not selecting this peptide as a potential vaccine candidate. However, a comparison of gp160 amino acid sequences from 245 different HIV isolates has shown that as little as five different consensus sequences can be defined on a serological basis among all the viral isolates (LaRosa et al., 1990). Therefore, the inventors propose that a cocktail of CTL-inducing peptides from V3-loop regions encompassing all the principal HIV groups (which may be five or less) may be sufficient for generating CTLs specific for cells expressing gp120 from most if not all HIV strains. Such a mixture would then serve as a prototype vaccine for evaluation for prevention of HIV infection of humans.

EXAMPLE 6—Rapid assay of influenza virus-specific CTLs

The protocol developed for the induction of HIV-specific CTLs was believed to be generally applicable to the identification, selection and assay of any peptide with unknown epitope specificity, for its ability to prime CTLs in vivo. Accordingly, the in vivo peptide-induction of CTLs specific for influenza virus was examined. Deres et al., (1989) had previously shown that a synthetic peptide R⁻, TYQRTRALVTG (aa 147–158), corresponding to a portion of the nucleoprotein of influenza virus, could prime influenza virus-specific CTLs in mice in vivo only when covalently linked through the N-terminus to tripalmitoyl-S-glycerylcysteinyl-seryl-serine ($P_3CSS$). However, using the protocol described above, specific CD8⁺ CTLs, that lysed target cells pre-treated with this peptide, could be induced in vivo by immunisation with the free synthetic peptide (TABLE 6).

TABLE 6

In vivo priming of peptide specific CTLs in Balb/c mice with a free synthetic peptide (B106) from influensa virus nucleoprotein

| Treatment To Effector Cells | Target Cells | % specific lysis at various E:T[a] ratios | | | |
|---|---|---|---|---|---|
| | | 160:1 | 80:1 | 40:1 | 20:1 |
| No Treatment | P815[b] | 5.7 | 0 | 0 | 2.5 |
| No Treatment | P815 + B106[c] | 83.9 | 76.6 | 57.1 | 47.3 |
| No Treatment | P815 + B105[d] | 11.0 | 26.0 | 19.3 | 16.0 |
| + Complement | P815 + B106 | 83.3 | 73.6 | 58.2 | 39.7 |
| + anti-CD4 + C | P815 + B106 | 67.2 | 59.3 | 40.7 | 25.8 |
| + anti-CD8 + C | P815 + B106 | 2.5 | 0 | 0 | 0.4 |
| + anti-CD4 | P815 + B106 | 64.8 | 67.9 | 44.7 | 24.8 |
| + anti-CD8 | P815 + B106 | 53.6 | 43.3 | 23.7 | 5.8 |
| No Treatment | 3A9[e] | 0 | 0 | ND | ND |
| No Treatment | 3A9 + B106[f] | 0 | 0 | 0 | 0 |

ND = Not Done
[a] = E:T = Effector to target cell ratio
[b] = MHC-matched target cells (H-2$^d$)
[c] = H-2$^d$ target cells pre-treated with Influenza virus peptide (ref. #4)
[d] = H-2$^d$ target cells pre-treated with Sendai virus peptide (ref. #5)
[e] = MHC-mis-matched target cells (H-2$^k$)
[f] = H-2$^k$ target cells pre-treated with Influenza virus peptide (ref. #4)

Thus, this method was indeed found to be useful in systems other than those related to the HIV virus. Furthermore, it is believed that this rapid screening method will have medical utility for developing candidate vaccines and therapeutics for various infectious diseases.

* * *

Changes may be made in the construction, operation and arrangement of the various parts, elements, steps and procedures described herein without departing from the concept and scope of the invention as defined in the claims.

REFERENCES

The following references are hereby incorporated by reference for the subject matter as specified in the specification and to the extent that they disclose, teach, enable or provide a basis for various aspects of the present invention.

Ahearne et al., III International Conference on AIDS, held in Washington, D.C., Jun. 1–5, 1987, abstract # M.10.3, page 8
Aichele, P. Hengartner, H. Zinkernagel, R. M. & Schulz, M. J., Exp. Med. 171:1815–1820 (1990)
Barnes, Science, 236:255 (1987)
Berzofsky et al., Nature, 334:706–708 (1988)
Berzofsky, J. A., FASEB J., 5:2412–2418 (1991)
Bodansky et al., Peptide Synthesis, John Wiley and Sons, Second Edition, 1976
Buller et al., Nature, 328:77 (1987)
Cease et al., Proc. Natl. Acad. Sci. USA, 84:4249–4253 (1987)
Click et al., Cellular Immunol. 3:264–276 (1972)
Coates et al., Nature, 326:549 (1987)
De Lisi & Berzofsky, Proc. Natl. Acad. Sci. USA, 82:7048 (1985)
Deres, K. Schild, H. Wiesmuller, K-H. Jung, G. & Rammensee, H-G., Nature 342:561–564 (1989)
Doherty et al., Adv. Cancer Res., 42:1 (1985)
Earl et al., Science, 234:728 (1986)
Fathman, Ann. Rev. Immunol., 5:477 (1987)
Fauci, A., AIDS Update 4:103 (1991).
Ho et al., J. Virol., 61:2024 (1987)
Hopp & Woods, J. Mol. Biol. 23:807 (1982)
Hopp, T. P., Mol. Immunol. 21:13–16 (1984).
Houghten, Proc. Natl. Acad. Sci, USA, 82:5131–5135 (1985)
Javaherian et al., Proc. Natl. Acad. Sci. U.S.A. 86:6768–6772 (1989)
Kaneshima, H. et al., Proc. Natl. Acad. Sci. U.S.A. 88:4523–4527 (1991).
Kast, W. M. et al., Proc. Natl. Acad. Sci. U.S.A. 88:2283–2287 (1991)
LaRosa, G. J. et al., Science 249:932–935 (1990)
Legrain et al., J. Virol., 60:1141 (1986)
Livingston & Fathman, Ann. Rev. Immunol. 5:477 (1987)
Maddon et al., Cell, 47:333 (1986)
Maizel et al., Eur. J. Immunol. 10:509, 1980
Maryanski, J. L. et al., Eur. J. Immunol. 15:1111–1117 (1985)
McOmie, J. F. W., Protective Groups in Organic Chemistry, Plenum Press, New York, 1973).
Merrifield, J. Am. Chem. Soc. 85:2149–2154 (1963)
Milich and McLachlan, Science, 234:1398, (1986)
Millich et al., J. Immunol. 134:4194–4203 (1985)
Milich et al., J. Exp. Med. 164:532 (1986)
Mittler, R. S. & Hoffman, M. K., Science 245:1380–1382 (1989).
Modrow et al., J. Virol., 61:570–578 (1987)
Naso et al., J. Virol., 45:1200, (1983)
Nixon, D. F. et al., Nature 336:484–487 (1988)
Platsoucas, C. D. & Good R., Proc. Natn. Acad. Sci. U.S.A. 78: 4500–4505 (1981)
Rees, Nature, 326:343 (1987)
Robey et al., Proc. Natl. Acad. Sci., USA 83:7023 (1986)
Sastry, K. J. & Arlinghaus, R. B., AIDS 5:699–707 (1991).
Senyk et al., J. Exp. Med., 133:1294 (1971)
Sette et al., Mol. Immunol., 23:807 (1986)
Siliciano, R. F. et al., Cell 54:561–575 (1988)
Takahashi, H. et al., Proc. Natn. Acad. Sci. U.S.A. 85:3105–3109 (1988)
Townsend, A. R. M. et al., Cell 44:959–968 (1986)
Wain-Hobson et al., Cell 40:9 (1985)
Walker et al., Science, 234:1563–1566 (1986)

Walker et al., Nature, 328:345 (1987)

Weinhold, K. J. et al., J. Immunol. 142:3091–3097 (1989).

What is claimed is:

1. A method of assaying a selected synthetically prepared peptide for its ability to induce a cytotoxic T cell response in an animal that has not previously been immunized with said peptide, said method comprising:
   (a) preparing a composition that includes a selected peptide suspected of being capable of inducing cytotoxic T lymphocytes (CTLs);
   (b) intradermally immunizing an animal with the composition;
   (c) recovering cytotoxic T cells from lymph nodes proximal to the site of intradermal immunization or which drain said site of said immunized animal; and
   (d) determining whether said cytotoxic T cells can lyse major histocompatibility complex (MHC)-matched target cells having said peptide or an antigen comprising said peptide on their surface.

2. The method of claim 1, wherein said animal is an experimental animal.

3. The method of claim 1, wherein the animal is immunized through a single injection of the composition.

4. The method of claim 1, wherein the animal is immunized through multiple injections of the composition at the same site.

5. The method of claim 1, wherein the peptide is free of an associated carrier molecule, lipid tail or T helper epitome.

6. The method of claim 1, wherein the composition is tested for its ability to induce a CTL response to a protein associated with a pathogen.

7. The method of claim 6, wherein the composition comprises a CTL-reactive peptide derived from an HIV protein.

8. The method of claim 1, wherein the degree of cytotoxic T cell activation is measured.

9. The method of claim 8 wherein activation of the cytotoxic T cells is measured by determining the cytolytic activity of said cells using major histocompatibility complex matched cells that express a targeted protein.

10. The method of claim 1, wherein the composition is further tested for its ability to elicit an antibody response.

11. A method of assaying a candidate peptide composition for its ability to induce a cytotoxic T cell response in an animal, said method comprising:
    (a) immunizing an animal through a single injection of the candidate peptide composition;
    (b) recovering cytotoxic T cells from lymph nodes proximal to the injection site of said immunized animal;
    (c) determining whether said cytotoxic T cells have been activated by the composition.

12. A method for preparing a pharmaceutical composition, comprising:
    (a) identifying a peptide composition capable of specifically priming CTLs, the peptide being identified by a method which includes:
    immunizing an animal with the peptide;
    recovering cytotoxic T cells from proximal to the injection site lymph nodes of said immunized animal;
    determining whether said cytotoxic T cells have been activated by the peptide; and
    (b) admixing the peptide with one or more pharmaceutically acceptable diluents or additives.

13. The method of claim 12, wherein the composition comprises a peptide or peptides derived from a natural protein or proteins, and said composition fails to elicit an antibody response against the natural protein or proteins.

14. The method of claim 12, wherein the composition comprises a peptide or peptides derived from a natural protein or proteins, and said composition further elicits an antibody response against the natural protein or proteins.

* * * * *

UNITED STATES PATENT AND TRADEMARK OFFICE
CERTIFICATE OF CORRECTION

PATENT NO. : 6,210,873 B1  
DATED : April 3, 2001  
INVENTOR(S) : Sastry et al.

Page 1 of 1

It is certified that error appears in the above-identified patent and that said Letters Patent is hereby corrected as shown below:

<u>Column 23, claim 7,</u>  
Line 29, please delete "epitome" and insert -- epitope -- therefor.

<u>Column 24, claim 12,</u>  
Lines 22-23, please delete "recovering cytotoxic T cells from proximal to the injection site lymph nodes of said immunized animal;" and insert -- recovering cytotoxic T cells from lymph nodes proximal to the injection site of said immunized animal; -- therefor.

Signed and Sealed this

First Day of January, 2002

*Attest:*

JAMES E. ROGAN
*Attesting Officer*     *Director of the United States Patent and Trademark Office*